(12) United States Patent
Bao et al.

(10) Patent No.: US 12,054,456 B2
(45) Date of Patent: Aug. 6, 2024

(54) PROCESSES FOR UPGRADING ALKANES AND ALKYL AROMATIC HYDROCARBONS

(71) Applicant: ExxonMobil Chemical Patents Inc., Baytown, TX (US)

(72) Inventors: Xiaoying Bao, Houston, TX (US); John S. Coleman, Seabrook, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/745,566

(22) Filed: May 16, 2022

(65) Prior Publication Data

US 2022/0281783 A1    Sep. 8, 2022

Related U.S. Application Data

(63) Continuation-in-part of application No. PCT/US2021/042165, filed on Jul. 19, 2021.
(Continued)

(51) Int. Cl.
*C07C 5/48* (2006.01)
*B01J 21/04* (2006.01)
(Continued)

(52) U.S. Cl.
CPC .............. *C07C 5/48* (2013.01); *B01J 21/04* (2013.01); *B01J 21/10* (2013.01); *B01J 23/002* (2013.01);
(Continued)

(58) Field of Classification Search
CPC ... C07C 5/48; C07C 2521/04; C07C 2521/10; C07C 2523/10; C07C 2523/14;
(Continued)

(56) References Cited

U.S. PATENT DOCUMENTS

| 4,788,371 A | 11/1988 | Imai et al. ............... 585/443 |
| 4,902,849 A * | 2/1990 | McKay ................. B01J 23/005 |
| | | 502/50 |

(Continued)

FOREIGN PATENT DOCUMENTS

| CN | 1041714 | 1/1990 | ........... C07C 5/3337 |
| EP | 0098622 | 3/1986 | ............ B01J 23/62 |

(Continued)

OTHER PUBLICATIONS

Morejudo, S. H. et al. (2016) "Direct Conversion of Methane to Aromatics in a Catalytic Co-ionic Membrane Reactor," *Science*, v.353(6299), pp. 563-556.

(Continued)

*Primary Examiner* — Thuan D Dang

(57) ABSTRACT

Processes for upgrading a hydrocarbon. The process can include introducing, contacting, and halting introduction of a hydrocarbon-containing feed into a reaction zone. The feed can be contacted with a catalyst within the reaction zone to effect dehydrogenation, dehydroaromatization, and/or dehydrocyclization of the feed to produce a coked catalyst and an effluent. The process can include introducing, contacting, and halting introduction of an oxidant into the reaction zone. The oxidant can be contacted with the coked catalyst to effect combustion of the coke to produce a regenerated catalyst. The process can include introducing, contacting, and halting introduction of a reducing gas into the reaction zone. The reduction gas can be contacted with the regenerated catalyst to produce a regenerated and reduced catalyst. The process can include introducing and contacting an additional quantity of the feed with the regenerated and reduced catalyst to produce a re-coked catalyst and additional first effluent.

26 Claims, 3 Drawing Sheets

| Reactor (n) | Reaction | | Regeneration | | Reduction |
|---|---|---|---|---|---|
| Reactor (n+1) | Reaction | Regeneration | | Reduction | Reaction |
| Reactor (n+2) | Regen | Reduction | Reaction | | Regen |
| Reactor (n+3) | Regen | | Reduction | Reaction | Regen |
| | | Time | | | |
| Reactor (n+4) | Re-activation | | | Reduction | Reaction |

Related U.S. Application Data

(60) Provisional application No. 63/062,084, filed on Aug. 6, 2020.

(51) Int. Cl.
*B01J 21/10* (2006.01)
*B01J 23/00* (2006.01)
*B01J 23/10* (2006.01)
*B01J 23/14* (2006.01)
*B01J 23/42* (2006.01)

(52) U.S. Cl.
CPC .............. *B01J 23/10* (2013.01); *B01J 23/14* (2013.01); *B01J 23/42* (2013.01); *C07C 2521/04* (2013.01); *C07C 2521/10* (2013.01); *C07C 2523/10* (2013.01); *C07C 2523/14* (2013.01); *C07C 2523/42* (2013.01)

(58) Field of Classification Search
CPC ............ C07C 2523/42; C07C 2523/04; C07C 2523/62; C07C 5/3337; B01J 21/04; B01J 21/10; B01J 23/002; B01J 23/10; B01J 23/14; B01J 23/42; B01J 35/10; B01J 37/0036; B01J 37/08; B01J 37/18; B01J 29/084; B01J 23/626; B01J 23/63; B01J 37/0201; B01J 37/088; Y02P 20/52; Y02P 20/584

See application file for complete search history.

(56) References Cited

U.S. PATENT DOCUMENTS

| | | | | |
|---|---|---|---|---|
| 4,962,265 | A | 10/1990 | De Clippeleir et al. | 585/660 |
| 5,633,421 | A | 5/1997 | Iezzi et al. | 585/660 |
| 5,817,596 | A | 10/1998 | Akporiaye et al. | 502/327 |
| 5,922,925 | A | 7/1999 | Akporiaye et al. | 585/660 |
| 6,313,063 | B1 * | 11/2001 | Rytter | C07C 5/325 502/355 |
| 6,582,589 | B2 | 6/2003 | Rytter et al. | 208/134 |
| 6,967,182 | B1 | 11/2005 | Olsbye et al. | 502/84 |
| 7,678,956 | B2 | 3/2010 | Heinritz-Adrian | 585/659 |
| 8,653,317 | B2 | 2/2014 | Pierce et al. | 585/659 |
| 9,091,433 | B2 | 7/2015 | Mabande et al. | |
| 9,725,380 | B2 | 8/2017 | Fridman et al. | C07C 5/3332 |
| 2003/0139637 | A1 | 7/2003 | Rytter et al. | 585/658 |
| 2004/0029729 | A1 | 2/2004 | Rytter et al. | 502/341 |
| 2005/0003960 | A1 | 1/2005 | Rytter et al. | 502/335 |
| 2015/0099914 | A1 | 4/2015 | Garza et al. | C07C 2/76 |
| 2016/0318828 | A1 | 11/2016 | Washburn et al. | C07C 5/3335 |
| 2017/0033889 | A1 | 2/2017 | Ma et al. | |
| 2017/0121251 | A1 | 5/2017 | Iaccino et al. | C07C 5/373 |
| 2017/0333889 | A1 * | 11/2017 | Clancy-Jundt | C07C 5/3337 |
| 2018/0312451 | A1 | 11/2018 | Schwint et al. | C07C 5/333 |

FOREIGN PATENT DOCUMENTS

| | | | |
|---|---|---|---|
| EP | 1016641 | 7/2000 | B01J 23/00 |
| EP | 1073516 | 2/2001 | B01J 21/10 |
| WO | WO2016/187249 | 11/2016 | C07C 2/76 |
| WO | WO2017/078894 | 5/2017 | C07C 5/333 |
| WO | WO2018/193668 | 10/2018 | B01J 23/62 |
| WO | WO2021/225747 | 11/2021 | C07C 5/333 |

OTHER PUBLICATIONS

Reichle, W. T. (1985) "Catalytic Reactions by Thermally Activated, Synthetic, Anionic Clay Minerals," *Jrnl. Catalysis*, v.94(2), pp. 547-557.

Schaper, H. et al. (1989) "Stabilized Magnesia: A Novel Catalyst (support) Material," *Applied Catalysis*, v.54(1), pp. 79-90.

Teleki, A. et al. (2008) "Distinguishing Between Aggregates and Agglomerates of Flame-Made $TiO_2$ by High-Pressure Dispersion," *Powder Tech.*, v.181(3), pp. 292-300.

Ziaka, Z. D. et al. (1993) "A High Temperature Catalytic Membrane Reactor for Propane Dehydrogenation," *Jrnl. Membrane Sci.*, v.77(2-3), pp. 221-232.

* cited by examiner

PROCESSES FOR UPGRADING ALKANES AND ALKYL AROMATIC HYDROCARBONS

CROSS-REFERENCE TO RELATED APPLICATION

This application is a continuation-in-part of co-pending International Application No. PCT/US2021/042165, filed on Jul. 19, 2021, and published as WO2022/031423, which claims priority to and the benefit of U.S. Provisional Application No. 63/062,084, filed on Aug. 6, 2020, the disclosures of which are incorporated herein by reference in their entireties.

FIELD

This disclosure relates to processes for upgrading alkanes and/or alkyl aromatic hydrocarbons. More particularly, this disclosure relates to processes for dehydrogenating, dehydroaromatizing, and/or dehydrocyclizing one or more alkanes and/or one or more alkyl aromatic hydrocarbons in the presence of a catalyst to produce an effluent that includes one or more upgraded hydrocarbons.

BACKGROUND

Catalytic dehydrogenation, dehydroaromatization, and dehydrocyclization of alkanes and/or alkyl aromatic hydrocarbons are industrially important chemical conversion processes that are endothermic and equilibrium-limited. The dehydrogenation of alkanes, e.g., $C_2$-$C_{16}$ alkanes, and/or alkyl aromatic hydrocarbons, e.g., ethylbenzene, can be done through a variety of different supported catalyst particle systems such as the Pt-based, Cr-based, Ga-based, V-based, Zr-based, In-based, W-based, Mo-based, Zn-based, and Fe-based systems. Among the existing propane dehydrogenation processes, a certain process uses an alumina supported chromia catalyst that provides one of the highest propylene yields at approximately 50% (55% propane conversion at 90% propylene selectivity), which is obtained at a temperature of approximately 560° C. to 650° C. and at a low pressure of 20 kPa-absolute to 50 kPa-absolute. It is desirable to increase the propylene yield without having to operate at such low pressure to increase the efficiency of the dehydrogenation process.

Increasing the temperature of the dehydrogenation process is one way to increase the conversion of the process according to the thermodynamics of the process. For example, at 670° C., 100 kPa-absolute, in the absence of any inert/diluent, the equilibrium propylene yield has been estimated via simulation to be approximately 74%. At such high temperature, however, the catalyst particles deactivate very rapidly and/or the propylene selectivity becomes uneconomically low. The rapid deactivation of the catalyst particles is believed to be caused by coke depositing onto the catalyst particles and/or agglomeration of the active phase. Coke can be removed by combustion using an oxygen-containing gas, however, agglomeration of the active phase is believed to be exacerbated during the combustion process, which rapidly reduces the activity and stability of the catalyst particles.

There is a need, therefore, for improved processes for dehydrogenating, dehydroaromatizing, and/or dehydrocyclizing alkanes and/or alkyl aromatic hydrocarbons. This disclosure satisfies this and other needs.

SUMMARY

Processes for upgrading alkanes and/or alkyl aromatic hydrocarbons are provided. In some embodiments, the process can include (I) introducing a hydrocarbon-containing feed that can include one or more of $C_2$-$C_{16}$ linear or branched alkanes, one or more of $C_4$-$C_{16}$ cyclic alkanes, one or more of $C_8$-$C_{16}$ alkyl aromatics, or a mixture thereof into a reaction zone. The process can also include (II) contacting the hydrocarbon-containing feed with a catalyst disposed within the reaction zone to effect at least one of dehydrogenation, dehydroaromatization, and dehydrocyclization of at least a portion of the hydrocarbon-containing feed to produce a coked catalyst and a first effluent that can include one or more upgraded hydrocarbons and molecular hydrogen. The hydrocarbon-containing feed and the catalyst can be contacted at a temperature in a range from 300° C. to 900° C., for a time period of 1 minute to 90 minutes, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. The catalyst can include a Group 8-10 element or a compound thereof disposed on a support. The process can also include (III) halting introduction of the hydrocarbon-containing feed into the reaction zone; (IV) introducing an oxidant into the reaction zone; (V) contacting the oxidant with the coked catalyst to effect combustion of at least a portion of the coke to produce a regenerated catalyst lean in coke and a second effluent comprising a combustion gas, where the oxidant and the coked catalyst are contacted for a time period of 1 minute to 90 minutes; and (VI) halting introduction of the oxidant into the reaction zone. The process can also include (VII) introducing a reducing gas into the reaction zone; (VIII) contacting the reducing gas with the regenerated catalyst to produce a regenerated and reduced catalyst and a third effluent, where the reducing gas and the regenerated catalyst are contacted for a time period of 0.1 seconds to 90 minutes; and (IX) halting introduction of the reducing gas into the reaction zone. The process can also include (X) introducing an additional quantity of the hydrocarbon-containing feed into the reaction zone and (XI) contacting the additional quantity of the hydrocarbon-containing feed with the regenerated and reduced catalyst to produce a re-coked catalyst and additional first effluent. The additional quantity of the hydrocarbon-containing feed and the regenerated and reduced catalyst can be contacted at a temperature in a range from 300° C. to 900° C., for a time period of 1 minute to 90 minutes, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed.

In other embodiments, the process can include (I) a reaction interval that can include introducing and halting introduction of a hydrocarbon-containing feed into a reaction zone. The hydrocarbon-containing feed can include one or more of $C_2$-$C_{16}$ linear or branched alkanes, one or more of $C_4$-$C_{16}$ cyclic alkanes, one or more of $C_8$-$C_{16}$ alkyl aromatics, or a mixture thereof. The process can also include (II) a regeneration interval following the reaction interval, the regeneration interval can include introducing and halting introduction of an oxidant into the reaction zone. The process can also include (III) a reduction interval following the regeneration interval, the reduction interval can include introducing and halting introduction of a reducing gas into the reaction zone. The reaction interval can be restarted after the reduction interval. During introduction of the hydrocarbon-containing feed into the reaction zone, the hydrocarbon-containing feed can contact a catalyst disposed within the reaction zone to effect at least one of dehydrogenation, dehydroaromatization, and dehydrocyclization of at least a portion of the hydrocarbon-containing feed to produce a coked catalyst and a first effluent that can include one or more upgraded hydrocarbons and molecular hydrogen. The hydrocarbon-containing feed and the catalyst can be contacted at a temperature in a range from 300° C. to 900° C., for a time period of 1 minute to 90 minutes, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. During introduction of the oxidant into the reaction zone, the oxidant can contact the coked catalyst to effect combustion of at least a portion of the coke to produce a regenerated catalyst lean in coke and a second effluent that can include a combustion gas. The oxidant and the coked catalyst can be contacted for a time period of 1 minute to 90 minutes. During introduction of the reducing gas into the reaction zone, the reducing gas can contact the regenerated catalyst to produce a regenerated and reduced catalyst. The catalyst can include a Group 8-10 element or a compound thereof disposed on a support.

DETAILED DESCRIPTION

Figure 1:
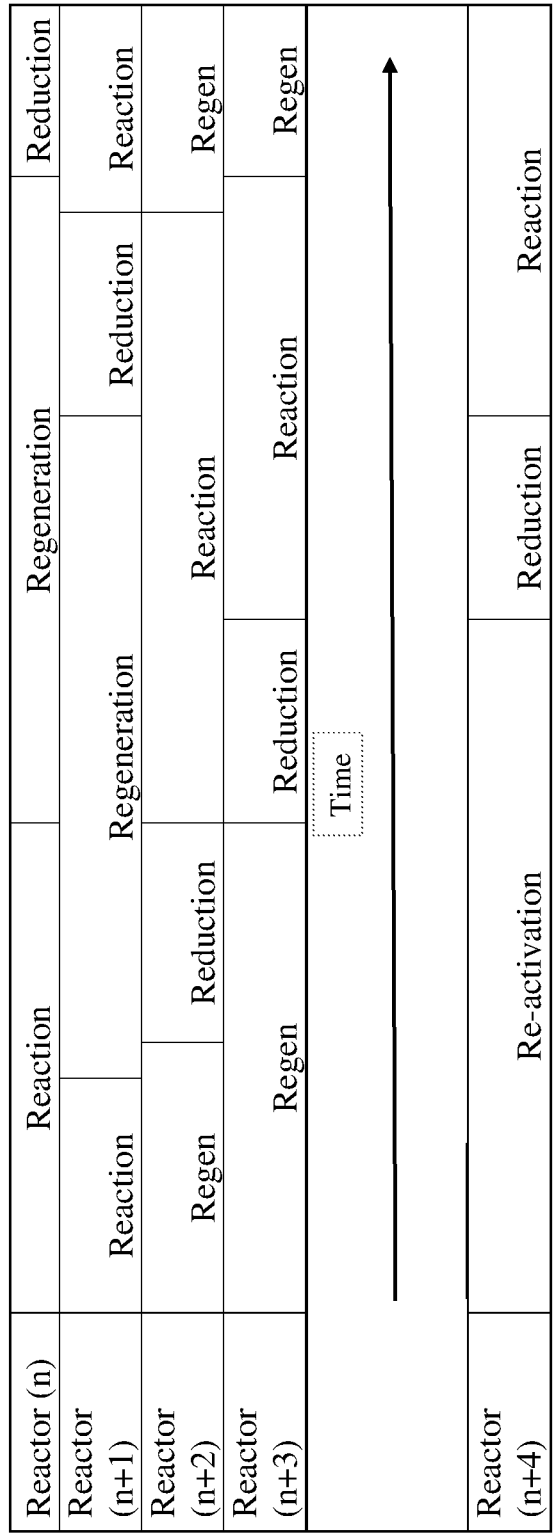
FIG. 1 depicts an illustrative time sequence for a plurality of reaction zones, according to one or more embodiments described.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for acquiring the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

The indefinite article "a" or "an", as used herein, means "at least one" unless specified to the contrary or the context clearly indicates otherwise. Thus, embodiments using "a reactor" or "a conversion zone" include embodiments where one, two or more reactors or conversion zones are used, unless specified to the contrary or the context clearly indicates that only one reactor or conversion zone is used.

The terms "up" and "down"; "upward" and "downward"; "upper" and "lower"; "upwardly" and "downwardly"; "above" and "below"; and other like terms used herein refer to relative positions to one another and are not intended to denote a particular spatial orientation since the apparatus and methods of using the same may be equally effective at various angles or orientations.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a $C_2$ hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

For the purposes of this disclosure, the nomenclature of elements is pursuant to the version of the Periodic Table of Elements (under the new notation) as provided in Hawley's Condensed Chemical Dictionary, 16$^{th}$ Ed., John Wiley & Sons, Inc., (2016), Appendix V. For example, a Group 8 element can include one or more of Fe, Ru, and Os, a Group 9 element can include one or more of Co, Rh, and Ir, and a group 10 element can include one or more of Ni, Pd, and Pt. The term "metalloid", as used herein, refers to the following elements: B, Si, Ge, As, Sb, Te, and At. In this disclosure, when a given element is indicated as present, it can be present in the elemental state or as any chemical compound thereof, unless it is specified otherwise or clearly indicated otherwise by the context.

The term "alkane" means a saturated hydrocarbon. The term "cyclic alkane" means a saturated hydrocarbon comprising a cyclic carbon ring in the molecular structure thereof. An alkane can be linear, branched, or cyclic.

The term "aromatic" is to be understood in accordance with its art-recognized scope, which includes alkyl substituted and unsubstituted mono- and polynuclear compounds.

The term "rich" when used in phrases such as "X-rich" or "rich in X" means, with respect to an outgoing stream obtained from a device, e.g., a conversion zone, that the stream comprises material X at a concentration higher than in the feed material fed to the same device from which the stream is derived. The term "lean" when used in phrases such as "X-lean" or "lean in X" means, with respect to an outgoing stream obtained from a device, e.g., a conversion zone, that the stream comprises material X at a concentration lower than in the feed material fed to the same device from which the stream is derived.

The term "mixed metal oxide" refers to a composition that includes oxygen atoms and at least two different metal atoms that are mixed on an atomic scale. For example, a "mixed Mg/Al metal oxide" has O, Mg, and Al atoms mixed on an atomic scale and is substantially the same as or identical to a composition obtained by calcining an Mg/Al hydrotalcite that has the general chemical formula

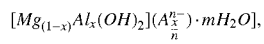

where A is a counter anion of a negative charge n, x is in a range of from >0 to <1, and m is ≥0. A material consisting of nm sized MgO particles and nm sized Al$_2$O$_3$ particles mixed together is not a mixed metal oxide because the Mg and Al atoms are not mixed on an atomic scale but are instead mixed on a nm scale.

The term "selectivity" refers to the production (on a carbon mole basis) of a specified compound in a catalytic reaction. As an example, the phrase "an alkane hydrocarbon conversion reaction has a 100% selectivity for an olefin hydrocarbon" means that 100% of the alkane hydrocarbon (carbon mole basis) that is converted in the reaction is converted to the olefin hydrocarbon. When used in connection with a specified reactant, the term "conversion" means the amount of the reactant consumed in the reaction. For example, when the specified reactant is propane, 100% conversion means 100% of the propane is consumed in the reaction. Yield (carbon mole basis) is conversion times selectivity. In another example, when the specified reactant is propane, if one mole of propane converts to one mole of methane and one mole of ethylene, the selectivity to methane is 33.3% and the selectivity to ethylene is 66.7%.

As used herein, the term "reactor" refers to any vessel(s) in which a chemical reaction occurs. The term "reactor" includes both distinct reactors, as well as reaction zones within a single reactor apparatus and, as applicable, reaction zones across multiple reactors. In other words and as is common, a single reactor may have a single reaction zone or multiple reaction zones. Where the description refers to a first and second reactor, it should be readily recognized that such reference includes two reactors, as well as a single reactor having first and second reaction zones. Likewise, a first reactor effluent and a second reactor effluent will be recognized to include the effluent from the first reaction zone and the second reaction zone of a single reactor, respectively.

As used herein, the term "fluidized bed" reactor refers to a reaction zone in which a plurality of discrete particles (e.g., catalyst particles) is contacted with a gas, where the gas flows such that the superficial gas velocity is sufficient to fluidize the discrete particles (i.e., above the minimum fluidization velocity) and is below the velocity required for dilute-phase pneumatic conveying of the discrete particles in order to maintain a solids bed with a void fraction below 95%. Locus of minimum fluidization velocity is described in, for example, Kunii, D., Levenspiel, O., Chapter 3 of Fluidization Engineering, 2$^{nd}$ Edition, Butterworth-Heinemann, Boston, 1991, and Walas, S. M., Chapter 6 of Chemical Process Equipment, Revised 2$^{nd}$ Edition, Butterworth-Heinemann, Boston, 2010.

As used herein, the term "fixed bed" refers to a catalyst bed disposed within the reaction zone (such as, vertical or horizontal, cylindrical pipe, or a spherical vessel) and may include transverse (also known as cross flow), axial flow, and/or radial flow of gases therethrough, where solids (e.g., catalyst particles) are substantially immobilized within the reactor and gas flows such that the superficial velocity is below the velocity required to fluidize the solid particles (i.e., below the minimum fluidization velocity) and/or the gas is moving in a downward direction so that solid particle fluidization is not possible.

As used herein, the terms "cyclical", "cyclic", and "cycle" are used interchangeably and refer to a periodic recurring or repeating event that occurs. In some embodiments, reactors can be cyclically operated to have a reaction interval, a regeneration interval, and a reduction interval. The duration and/or order of the interval steps may change over time. In other embodiments, reactors can be cyclically operated to have the reaction interval, the regeneration interval, the reduction interval, and periodically, e.g., every 12 hours to 90 days, the regeneration interval can be replaced with a re-activation interval. The regeneration interval, during normal operation, can contact the coked catalyst with the oxidant at a normal temperature, a normal pressure, and for a normal period of time. During the re-activation interval, which can occur every 12 hours to every 90 days, one or more process conditions during the regeneration interval can be modified to accomplish the re-activation interval. For example, the normal temperature can be increased, the normal pressure can be increased, and/or the normal period of time of the regeneration interval can be increased to effect the re-activation of the coked catalyst. In some embodiments, the re-activation interval can be used to more fully regenerate the coked catalyst particles than typically occurs during the regeneration interval during normal operation.

Overview

The hydrocarbon-containing feed can be or can include, but is not limited to, one or more alkanes, e.g., C$_2$-C$_{16}$ linear or branched alkanes and/or C$_4$-C$_{16}$ cyclic alkanes, and/or one or more alkyl aromatic hydrocarbons, e.g., C$_8$-C$_{16}$ alkyl aromatic hydrocarbons. In some embodiments, the hydrocarbon-containing feed can optionally include 0.1 vol %, 1 vol %, or 5 vol % to 10 vol %, 15 vol %, 20 vol %, 30 vol %, 40 vol %, or 50 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include <0.1 vol % of steam or can be free of steam, based on the total volume of any $C_2$-$C_{16}$ alkanes and any $C_8$-$C_{16}$ alkyl aromatic hydrocarbons in the hydrocarbon-containing feed. The hydrocarbon-containing feed can be contacted with a catalyst disposed within the reaction zone to effect at least one of dehydrogenation, dehydroaromatization, and dehydrocyclization of at least a portion of the hydrocarbon-containing feed to produce a coked catalyst and a first effluent that can include one or more upgraded hydrocarbons and molecular hydrogen. The hydrocarbon-containing feed and the catalyst can be contacted at a temperature in a range from 300° C. to 900° C., for a first time period of 1 minute to 90 minutes, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. The catalyst can include one or more Group 8-10 elements, e.g., Pt, disposed on a support. In some embodiments, the catalyst can include from 0.001 wt % to 6 wt % of the Group 8-10 element, based on the weight of the support. The support can be or can include, but is not limited to, a Group 2 element, a Group 4 element, a Group 12 element, an element having an atomic number of 21, 39, or 57-71, or a compound thereof.

After the first time period, introduction of the hydrocarbon-containing feed can be halted and one or more oxidants can be introduced into the reaction zone. The oxidant can contact the coked catalyst to effect combustion of at least a portion of the coke to produce a regenerated catalyst lean in coke and a second effluent that can include a combustion gas. The oxidant and the coked catalyst can be contacted for a second time period of 1 minute to 90 minutes. After the second time period, introduction of the oxidant can be halted and one or more reducing gases can be introduced into the reaction zone. The reducing gas can contact the regenerated catalyst to produce a regenerated and reduced catalyst and a third effluent. The reducing gas and the regenerated catalyst can be contacted for a third time period of 0.1 seconds to 90 minutes. After the third time period, introduction of the reducing gas can be halted and an additional quantity of the hydrocarbon-containing feed can be introduced into the reaction zone to produce re-coked catalyst and an additional quantity of the first effluent.

In other embodiments, the process for upgrading a hydrocarbon can include a reaction interval that can include introducing and halting introduction of the hydrocarbon-containing feed into the reaction zone, a regeneration interval following the reaction interval that can include introducing and halting introduction of the oxidant into the reaction zone, and a reduction interval following the regeneration interval that can include introducing and halting introduction of the reducing gas into the reaction zone. The reaction interval can be restarted after the reduction interval.

It has been surprisingly and unexpectedly discovered that the catalyst that includes a Group 8-10 element, e.g., Pt, disposed on the support can remain sufficiently active and stable after many cycles, e.g., at least 15, at least 20, at least 30, at least 40, at least 50, at least 60, at least 70, at least 100 cycles, at least 125 cycles, at least 150 cycles, at least 175 cycles, or at least 200 cycles with each cycle time lasting for ≤5 hours, ≤4 hours, ≤3 hours, ≤2 hours, ≤1 hour, ≤50 minutes, ≤45 minutes, ≤30 minutes, ≤15 minutes, ≤10 minutes, ≤5 minutes, ≤1 minute, ≤30 seconds, or ≤10 seconds. In some embodiments, the cycle time can be from 5 seconds, 30 seconds, 1 minute or 5 minutes to 10 minutes, 20 minutes, 30 minutes, 45 minutes, 50 minutes, 70 minutes, 2 hours, 3 hours, 4 hours, or 5 hours. In some embodiments, after the catalyst performance stabilizes (sometimes the few first cycle can have a relatively poor or relatively good performance, but the performance can eventually stabilize), the process can produce a first upgraded hydrocarbon product yield, e.g., propylene when the hydrocarbon-containing feed includes propane, at an upgraded hydrocarbon selectivity, e.g., propylene, of ≥75%, ≥80%, ≥85%, or ≥90%, or >95% when initially contacted with the hydrocarbon-containing feed, and can have a second upgraded hydrocarbon product yield upon completion of the last cycle (at least 15 cycles total) that can be at least 90%, at least 93%, at least 95%, at least 97%, at least 98%, at least 99%, at least 99.5%, or at least 100% of the first upgraded hydrocarbon product yield at an upgraded hydrocarbon selectivity, e.g., propylene, of ≥75%, ≥80%, ≥85%, or ≥90%, or >95%. Prior to this discovery, it was believed that catalysts having a Group 8-10 element, e.g., Pt, as the active component would not maintain sufficient activity and stability when subjected to so many short cycles with a simple oxidative regeneration that requires no addition of halogen.

The first cycle begins upon contact of the catalyst with the hydrocarbon-containing feed, followed by contact with the oxidant to produce the regenerated catalyst, followed by contact with the reducing gas to produce the regenerated and reduced catalyst, and the first cycle ends and a second cycle begins upon contact of the regenerated and reduced catalyst with the additional quantity of the hydrocarbon-containing feed. The second cycle ends and the third and each subsequent cycle begins upon contact of the regenerated and reduced catalyst and the additional quantity of the hydrocarbon-containing feed and the third and each subsequent cycle ends and the next begins upon contact of additional or subsequently regenerated and reduced catalyst with the additional quantity of the hydrocarbon-containing feed.

Furthermore, very high propylene yields have been obtained via the processes and catalysts described herein. In some embodiments, when the hydrocarbon-containing feed includes propane and the upgraded hydrocarbon includes propylene, contacting the hydrocarbon-containing feed with the catalyst can produce a propylene yield of at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, or at least 69% at a propylene selectivity of at least 75%, at least 80%, at least 85%, at least 90%, or at least 95%. In other embodiments, when the hydrocarbon-containing feed includes at least 70 vol % of propane, based on a total volume of the hydrocarbon-containing feed, contacting the hydrocarbon-containing feed with the catalyst under a propane partial pressure of at least 20 kPa-absolute, a propylene yield of at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, or at least 69% at a propylene selectivity of at least 75%, at least 80%, at least 85%, at least 90%, or at least 95% can be obtained. It is believed that the propylene yield can be further increased to at least 70%, at least 72%, at least 75%, at least 77%, at least 80%, or at least 82% at a propylene selectivity of at least 75%, at least 80%, at least 85%, at least 90%, or at least 95%.

In some embodiments, when the hydrocarbon-containing feed includes propane and the upgraded hydrocarbon includes propylene, contacting the hydrocarbon-containing feed with the catalyst can produce a propylene yield of at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, or at least 63% at a propylene selectivity of at least 75%, at least 80%, at least 85%, at least 90%, or at least 95% for at least 15, at least 20, at least 30, at least 40, at least 50, at least 60, at least 70, at least 100 cycles, at least 125 cycles, at least 150 cycles, at least 175 cycles, or at least 200 cycles. In other embodiments, when a hydrocarbon-containing feed includes at least 70 vol % of propane, based on a total volume of the hydrocarbon-containing feed, is contacted under a propane partial pressure of at least 20 kPa-absolute, a propylene yield of at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, or at least 63% at a propylene selectivity of at least 75%, at least 80%, at least 85%, at least 90%, or at least 95% can be obtained for at least 15, at least 20, at least 30, at least 40, at least 50, at least 60, at least 70, at least 100 cycles, at least 125 cycles, at least 150 cycles, at least 175 cycles, or at least 200 cycles. It is believed that the propylene yield can be further increased to at least 65%, at least 67%, at least 68%, at least 70%, at least 72%, at least 75%, at least 77%, at least 80%, or at least 82% at a propylene selectivity of at least 75%, at least 80%, at least 85%, at least 90%, or at least 95% for at least 15 cycles, at least 20, at least 30, at least 40, at least 50, at least 60, at least 70, at least 100 cycles, at least 125 cycles, at least 150 cycles, at least 175 cycles, or at least 200 cycles by further optimizing the composition of the support and/or adjusting one or more process conditions. In some embodiments, the propylene yield can be obtained when the catalyst is contacted with the hydrocarbon feed at a temperature of at least 620° C., at least 630° C., at least 640° C., at least 650° C., at least 655° C., at least 660° C., at least 670° C., at least 680° C., at least 690° C., at least 700° C., or at least 750° C. for at least 15, at least 20, at least 30, at least 40, at least 50, at least 60, at least 70, at least 100 cycles, at least 125 cycles, at least 150 cycles, at least 175 cycles, or at least 200 cycles. Such a high propylene yield under such processing conditions was not thought possible.

Hydrocarbon Upgrading Process

The hydrocarbon-containing feed can be contacted with the catalyst particles within any suitable conversion or reaction zone to effect one or more of dehydrogenation, dehydroaromatization, and dehydrocyclization of at least a portion of the hydrocarbon-containing feed to produce the conversion effluent that can include the coked catalyst particles, the one or more upgraded hydrocarbons, and the molecular hydrogen. In some embodiments, the catalyst can be disposed in a fixed bed within the reaction zone. In other embodiments, the catalyst can be in the form of a plurality of discrete particles within the reaction zone. When the catalyst is in the form of a plurality of discrete particles within the reaction zone, a flow of the hydrocarbon-containing feed through the reaction zone, a flow of the oxidant through the reaction zone, a flow of the reducing gas through the reaction zone, and a flow of any other gas through the reaction zone, e.g., a stripping gas used to remove at least a portion of any residual hydrocarbon-containing feed, first effluent, oxidant, second effluent, reducing gas, and/or third effluent from the reaction zone, can be such that a superficial gas velocity is sufficient to fluidize the plurality of discrete particles but is below a velocity required for dilute-phase pneumatic conveying of the plurality of discrete particles in order to maintain a catalyst bed with a void fraction below 95%.

Any number of reaction zones can be operated in series and/or in parallel. Any two or more types of reaction zones can be used in combination with one another. If two or more reaction zones are used the reaction zones can be operated at the same conditions and/or at different conditions and can receive the same hydrocarbon-containing feed or different hydrocarbon-containing feeds. If two or more reaction zones are used, the reaction zones can be arranged in series, in parallel, or a combination thereof with respect to one another. In some embodiments, at least three reaction can be operated in parallel. For example, the first reaction zone can include a first catalyst disposed therein, the second reaction zone can include a second catalyst disposed therein, and the third reaction zone can include a third catalyst disposed therein. In some embodiments, the first reaction zone, the second reaction zone, and the third reaction zone can be operated in parallel, where a timing of the introduction of the hydrocarbon-containing feed, the oxidant, and the reducing gas between the first, second, and third reaction zones can be such that there is a continuous production of the one or more upgraded hydrocarbons and molecular hydrogen across the first, second, and third reaction zones. As noted above, it should be understood that the first, second, third, and any additional reaction zones can be disposed within a single vessel or reactor, separate vessels or reactors, or a combination thereof. In some embodiments, at least 3, 4, 5, 6, 7, 8, 9, 10, or more reaction zones can be operated in parallel.

FIG. 1 depicts an illustrative time sequence for a plurality of reaction zones, according to one or more embodiments. More particularly, one cyclic arrangement of various reaction zones is shown, where a first, second, and third reaction zone alternate between reaction intervals, regeneration intervals, and reduction intervals, while a fourth reaction zone undergoes a re-activation interval in place of the regeneration interval. As described above, the regeneration interval, during normal operation, can contact the coked catalyst with the oxidant at a normal temperature, a normal pressure, and for a normal period of time. During the re-activation interval, which can occur every 12 hours to every 90 days, one or more process conditions during the regeneration interval can be modified to accomplish the re-activation interval. For example, the normal temperature can be increased, the normal pressure can be increased, and/or the normal period of time of the regeneration interval can be increased to effect the re-activation of the coked catalyst. In some embodiments, the re-activation interval can be used to more fully regenerate the coked catalyst particles than typically occurs during the regeneration interval during normal operation.

In some embodiments, when two or more reaction zones are operated in parallel, the process conditions within each reaction zone can be the same or substantially the same. In other embodiments, when two or more reaction zones are operated in parallel, the process conditions within each reaction zone can be different. As such, in some embodiments, a first hydrocarbon-containing feed, e.g., propane, can be introduced into a first reaction zone and a second hydrocarbon-containing feed, e.g., isobutane, can be introduced into a second reaction zone and the process conditions can be tailored to produce the desired upgraded hydrocarbon, e.g., propylene in the first reaction zone and isobutylene in the second reaction zone.

The hydrocarbon-containing feed and catalyst can be contacted within the reaction zone at a temperature in a range from 300° C., 350° C., 400° C., 450° C., 500° C., 550° C., 600° C., 620° C., 650° C., 660° C., 670° C., 680° C., 690° C., or 700° C. to 725° C., 750° C., 760° C., 780° C., 800° C., 825° C., 850° C., 875° C., or 900° C. In some embodiments, the hydrocarbon-containing feed and catalyst can be contacted at a temperature of at least 620° C., at least 650° C., at least 660° C., at least 670° C., at least 680° C., at least 690° C., or at least 700° C. to 725° C., 750° C., 760° C., 780° C., 800° C., 825° C., 850° C., 875° C., or 900° C. The hydrocarbon-containing feed can be introduced into the reaction zone and contacted with the catalyst therein for a time period of 1 minute, 3 minutes, 5 minutes, 7 minutes, or 10 minutes to 20 minutes, 30 minutes, 50 minutes, 70 minutes, or 90 minutes.

The hydrocarbon-containing feed and catalyst can be contacted under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. In some embodiments, the hydrocarbon partial pressure during contact of the hydrocarbon-containing feed and the catalyst can be in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute, where the hydrocarbon partial pressure is the total partial pressure of any $C_2$-$C_{16}$ alkanes and any $C_8$-$C_{16}$ alkyl aromatics in the hydrocarbon-containing feed.

In some embodiments, the hydrocarbon-containing feed can include at least 60 vol %, at least 65 vol %, at least 70 vol %, at least 75 vol %, at least 80 vol %, at least 85 vol %, at least 90 vol %, at least 95 vol %, or at least 99 vol % of a single $C_2$-$C_{16}$ alkane, e.g., propane, based on a total volume of the hydrocarbon-containing feed. The hydrocarbon-containing feed and catalyst can be contacted under a single $C_2$-$C_{16}$ alkane, e.g., propane, pressure of at least 20 kPa-absolute, at least 50 kPa-absolute, at least 100 kPa-absolute, at least 150 kPa-absolute, at least 250 kPa-absolute, at least 300 kPa-absolute, at least 400 kPa-absolute, at least 500 kPa-absolute, or at least 1,000 kPa-absolute.

The hydrocarbon-containing feed can be contacted with the catalyst within the reaction or conversion zone at any weight hourly space velocity (WHSV) effective for carrying out the upgrading process. In some embodiments, the WHSV can be 0.01 hr$^{-1}$, 0.1 hr$^{-1}$, 1 hr$^{-1}$, 2 hr$^{-1}$, 5 hr$^{-1}$, 10 hr$^{-1}$, 20 hr$^{-1}$, 30 hr$^{-1}$, or 50 hr$^{-1}$ to 100 hr$^{-1}$, 250 hr$^{-1}$, 500 hr$^{-1}$, or 1,000 hr$^{-1}$.

In some embodiments, the hydrocarbon-containing feed can be or can include propane, the hydrocarbon-containing feed can be at a temperature in a range from 300° C. to 700° C. when introduced into the reaction zone, the hydrocarbon-containing feed can have a hydrocarbon partial pressure of 20 kPa-absolute to 1,000 kPa-absolute, and the first effluent can be at a temperature in a range from 500° C., 580° C., 600° C., 620° C., or 650° C. to 670° C., 690° C., 720° C., 750° C., 775° C., or 800° C. upon exiting the reaction zone. In other embodiments, upon exiting the reaction zone, the first effluent can be at a temperature of ≥580° C., more preferably ≥630° C., or more preferably ≥670° C.

In some embodiments, an inverse temperature profile can be maintained within the reaction zone during introduction of the hydrocarbon-containing feed. As used herein, the term "inverse temperature profile" means that the reaction zone inlet temperature is lower than the reaction zone outlet temperature. Preferably, a centerline temperature at the reaction zone inlet can be lower than a centerline temperature at the reaction zone outlet. "Inverse temperature profile" includes reaction zones in which the temperature varies in the reaction zone so long as the temperature at the reaction zone inlet is lower than the temperature at the reaction zone outlet. "Inverse temperature profile" further encompasses a reaction zone having a centerline temperature $T_1$, at some length along the reaction zone, the centerline temperature decreases to temperature $T_2$; at a further length along the reaction zone, the centerline temperature rises to temperature $T_3$; finally, the centerline temperature at the reaction zone outlet decreases to temperature $T_4$, where $T_3 > T_4 > T_1 > T_2$. In a preferred embodiment, the inverse temperature profile of within the reaction zone can be such that the temperature within the reaction zone increases from the reaction zone inlet to the reaction zone outlet. Maintaining an inverse temperature profile within the reaction zone may advantageously minimize cracking of the hydrocarbon feedstock (see, e.g., U.S. Provisional Patent Application No. 63/022,034, filed on May 8, 2020), minimize carbonaceous material formation at the inlet, which can contribute to coking of the catalyst. The inverse temperature profile may also provide sufficient reaction time and length in the reaction zone to produce a sufficient amount of molecular hydrogen, at lower operating temperatures than the outlet temperature, which can reduce or minimize carbonaceous material formation at the reaction zone outlet.

In some embodiments, an isothermal or substantially isothermal temperature profile be maintained within the reaction zone. An advantage of maintaining an isothermal temperature may be increased catalyst efficiency and improved product yield. As used herein, the term "isothermal temperature profile" means that the temperature at each point between the reactor inlet and reactor outlet as measured along a centerline of the reaction zone is kept essentially constant, e.g., at the same temperature or within the same narrow temperature range where the difference between an upper temperature and a lower temperature is no more than 40° C., more preferably no more than 20° C. In some embodiments, the isothermal temperature profile is one where the reactor inlet temperature is within about 40° C. of the reactor outlet temperature, alternatively within about 20° C., alternatively within about 10° C., alternatively within about 5° C., alternatively the reactor inlet temperature is the same as the reactor outlet temperature. In other embodiments, the isothermal temperature profile can be one where the reactor inlet temperature is within about 20% of the reactor outlet temperature, alternatively within about 10%, alternatively within about 5%, alternatively within about 1%.

In some embodiments, the hydrocarbon-containing feed can be or can include propane, the upgraded hydrocarbon be or can include propylene, and introduction of the hydrocarbon-containing feed into the reaction zone can be halted when the temperature of the first effluent upon exiting the reaction zone falls below 710° C., 680° C., 650° C., 620° C., 610° C., 600° C., 590° C., 580° C., 570° C., 560° C., or 550° C.

In some embodiments, the hydrocarbon-containing feed can be or can include propane, the upgraded hydrocarbon can be or can include propylene, contacting the hydrocarbon-containing feed with the catalyst within the reaction zone can have a propylene selectivity of ≥70%, ≥75%, ≥80%, 85%, or 90%, and introduction of the hydrocarbon-containing feed into the reaction zone can be halted when a propylene yield falls below 65%, 50%, 55%, 50%, 47%, 45%, 43%, 40%, 37%, or 35%.

After the introduction of the hydrocarbon-containing feed into the reaction has been halted, the oxidant can be introduced into and contacted with the coked catalyst to produce a regenerated catalyst and a second effluent that can include a combustion gas. The oxidant can be or can include, but is not limited to, molecular oxygen ($O_2$), ozone ($O_3$), carbon dioxide ($CO_2$), steam ($H_2O$), or a mixture thereof. In some embodiments, an amount of oxidant in excess of that needed to combust 100% of the coke on the catalyst can be used to increase the rate of coke removal from the catalyst, so that the time needed for coke removal can be reduced and lead to an increased yield in the upgraded product produced within a given period of time.

The coked catalyst and oxidant can be contacted with one another at a temperature in a range from 500° C., 550° C., 600° C., 650° C., 700° C., 750° C., or 800° C. to 900° C., 950° C., 1,000° C., 1,050° C., or 1,100° C. to produce the regenerated catalyst. In some embodiments, the coked catalyst and oxidant can be contacted with one another at a temperature in a range from 500° C. to 1,100° C., 600° C. to 1,000° C., 650° C. to 950° C., 700° C. to 900° C., or 750° C. to 850° C. to produce the regenerated catalyst. The coked catalyst and oxidant can be contacted with one another for a time period of 1 minute, 3 minutes, 5 minutes, 7 minutes, or 10 minutes to 20 minutes, 30 minutes, 50 minutes, 70 minutes, or 90 minutes. In some embodiments, the coked catalyst and oxidant can be contacted for a time period sufficient to remove ≥50 wt %, ≥75 wt %, or ≥90 wt % or >99% of any coke disposed on the catalyst.

In some embodiments, the time period the coked catalyst and oxidant contact one another can be less than, substantially the same, or greater than the time period the catalyst contacts the hydrocarbon-containing feed to produce the first effluent and the coked catalyst. For example, the time period the coked catalyst and oxidant contact one another can be at least 90%, at least 60%, at least 30%, or at least 10% less than the time period the catalyst contacts the hydrocarbon-containing feed to produce the effluent. In other embodiments, the time period the coked catalyst and oxidant contact one another can be greater than the time period the catalyst contacts the hydrocarbon-containing feed to produce the effluent and the coked catalyst. For example, the coked catalyst and oxidant contact one another can be at least 50%, at least 100%, at least 300%, at least 500%, at least 1,000%, at least 10,000% greater than the time period the catalyst contacts the hydrocarbon-containing feed to produce the effluent.

The coked catalyst and oxidant can be contacted with one another under an oxidant pressure in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute to produce the regenerated catalyst.

In some embodiments, in addition to the coked catalyst particles, one or more supplemental fuels can also be contacted with the oxidant within the reaction zone to effect combustion of at least a portion of the supplemental fuel to produce heat and additional combustion gas. In some embodiments, introduction of the fuel into the reaction zone in combination with the oxidant can produce heat that can heat the reaction zone to a temperature of ≥580° C., ≥620° C., ≥650° C., ≥680° C., ≥710° C., ≥740° C., ≥770° C., ≥800° C., ≥850° C., ≥900° C., or ≥1,000° C., or greater. The optional supplemental fuel can be or can include, but is not limited to, molecular hydrogen ($H_2$), methane ($CH_4$), ethane ($C_2H_6$), propane ($C_3H_8$), or a mixture thereof. The optional supplemental fuel can be mixed with an inert gas such as argon (Ar), neon (Ne), helium (He), molecular nitrogen ($N_2$), or a mixture thereof.

Without wishing to be bound by theory, it is believed that at least a portion of the Group 8-10 element, e.g., Pt, disposed on the coked catalyst can be agglomerated as compared to the catalyst prior to contact with the hydrocarbon-containing feed. It is believed that during combustion of at least a portion of the coke on the coked catalyst that at least a portion of the Group 8-10 element can be re-dispersed about the support. Re-dispersing at least a portion of any agglomerated Group 8-10 element can increase the activity and improve the stability of the catalyst over many cycles.

In some embodiments, at least a portion of the Group 8-10 element, e.g., Pt, in the regenerated catalyst can be at a higher oxidized state as compared to the Group 8-10 element in the catalyst contacted with the hydrocarbon-containing feed and as compared to the Group 8-10 element in the coked catalyst. As such, as noted above, the process can also include contacting the regenerated catalyst with a reducing gas to produce the regenerated and reduced catalyst. Suitable reducing gases (reducing agent) can be or can include, but are not limited to, molecular hydrogen ($H_2$), carbon monoxide (CO), methane ($CH_4$), ethane ($C_2H_6$), propane ($C_3H_8$), ethylene ($C_2H_4$), propylene ($C_3H_6$), steam, or a mixture thereof. In some embodiments, the reducing gas can be mixed with an inert gas such as argon (Ar), neon (Ne), helium (He), molecular nitrogen ($N_2$), carbon dioxide ($CO_2$), steam ($H_2O$), or a mixture thereof. In such embodiments, at least a portion of the Group 8-10 element in the regenerated and reduced catalyst can be reduced to a lower oxidation state, e.g., the elemental state, as compared to the Group 8-10 element in the regenerated catalyst. In this embodiment, the additional quantity of the hydrocarbon-containing feed can be contacted with at least a portion of the regenerated catalyst and/or at least a portion of the regenerated and reduced catalyst.

In some embodiments, the regenerated catalyst and the reducing gas can be contacted at a temperature in a range from 400° C., 450° C., 500° C., 550° C., 600° C., 620° C., 650° C., or 670° C. to 720° C., 750° C., 800° C., or 900° C. The regenerated catalyst and the reducing gas can be contacted for a time period in a range from 0.1 seconds, 0.5 seconds, 5 seconds, 10 seconds, 20 seconds, 30 seconds, or 1 minute to 10 minutes, 30 minutes, 60 minutes, or 90 minutes. The regenerated catalyst and reducing gas can be contacted at a reducing agent pressure in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute to produce the regenerated catalyst. In some embodiments, the reduction can be carried out at a higher temperature than the reaction, and the cooling rate from reduction to reaction can be >50° C./min, >200° C./min, >800° C./min, or >3,200° C./min. The regenerated and reduced catalyst can be contacted with an additional quantity of the hydrocarbon-containing feed within the reaction zone to produce additional effluent and additional coked catalyst.

In some embodiments, the oxidant can flow through the reaction zone in the same direction as the hydrocarbon-containing feed flows through the reaction zone. In other embodiments, the oxidant can flow through the reaction zone in the opposite direction as the hydrocarbon-containing feed. In some embodiments, the reducing gas can flow through the reaction zone in the same direction as the hydrocarbon-containing feed flows through the reaction zone. In other embodiments, the reducing gas can flow through the reaction zone in the opposite direction as the hydrocarbon-containing feed. As such, the oxidant and the reducing gas can independently flow through the reaction zone in the same direction or in the opposite direction as the hydrocarbon-containing feed.

In some embodiments, one or more additional feeds, e.g., one or more stripping gases or sweep fluids, can be utilized between flows of the hydrocarbon-containing feed and the oxidant, between the oxidant and the reducing gas, and/or between the reducing gas and the additional quantity of the hydrocarbon-containing feed. The stripping gas or sweep fluid can, among other things, purge or otherwise urge undesired material from the reaction zone, such as non-combustible particulates including soot, residual or entrained hydrocarbon-containing feed, first effluent, oxidant, second effluent, reducing gas, and/or third effluent. In some embodiments, the additional feed(s) can be inert under the dehydrogenation, dehydroaromatization, and dehydrocyclization, combustion, and/or reducing conditions. Suitable sweep fluids can be or can include, but are not limited to, $N_2$, He, Ar, $CO_2$, $H_2O$, $CO_2$, $CH_4$, or a mixture thereof. In some embodiments, if the process utilizes a sweep fluid the duration or time period the sweep fluid can be introduced into the reaction zone can be in a range from 1 second, 5 seconds, 10 seconds, 20 seconds, 30 seconds, or 1 minute to 10 minutes, 30 minutes, 60 minutes, or 90 minutes.

In some embodiments, at least a portion of any residual hydrocarbon-containing feed, first effluent, or both can be removed from the reaction zone before introduction of the oxidant by subjecting the reaction zone to a pressure of less than atmospheric pressure. Similarly, in some embodiments, at least a portion of any residual oxidant, second effluent, or both can be removed from the reaction zone before introduction of the reducing gas by subjecting the reaction zone to a pressure of less than atmospheric pressure. Similarly, in some embodiments, at least a portion of any residual reducing gas, third effluent, or both can be removed from the reaction zone before introduction of the additional quantity of hydrocarbon-containing feed by subjecting the reaction zone to a pressure of less than atmospheric pressure. In some embodiments a combination of introducing the stripping gas and subjecting the reaction zone to a pressure of less than atmospheric pressure can be used to remove at least a portion of any residual hydrocarbon-containing feed, first effluent, oxidant, second effluent, reducing gas, and/or third effluent from the reaction zone.

In some embodiments, one or more heat-storing materials can be disposed within the reaction zone. The heat-storing material can be inert or substantially inert such that the heat-storing material is not reactive during introduction of the hydrocarbon-containing feed, the oxidant, the reducing gas, and any stripping gas or sweep fluids into the reaction zone. The heat-storing material can release at least a portion of stored heat during introduction and contact of the hydrocarbon-containing feed with the catalyst. The heat-storing material can store heat producing during introduction and contact of the oxidant with the coked catalyst, during introduction and contact of the reducing gas with the regenerated catalyst, and/or during introduction of any stripping gas or sweep fluid. In some embodiments, the heat-storing material can be or can include, but is not limited to, quartz, silicon carbide, aluminum nitride, silicon nitride, boron carbide, alumina, or a mixture thereof.

In some embodiments, one or more heat-generating materials can be disposed within the reaction zone. The heat-generating material can be configured to generate heat during at least one step of the process, e.g., during contact of the hydrocarbon-containing feed with the catalyst, during contact of the oxidant with the coked catalyst, during contact of the reducing gas with the regenerated catalyst, and/or during introduction of any stripping gas or sweep fluid. In some embodiments, the heat-generating material can be or can include, but is not limited to, a metal in oxide form supported on a carrier. The metal can be or can include, but is not limited to, an alkali metal, an alkaline earth metal, copper, chromium, molybdenum, vanadium, cerium, yttrium, scandium, tungsten, manganese, iron, cobalt, nickel, silver, bismuth, or a mixture or combination thereof. The carrier can be or can include, but is not limited to, aluminum oxides, aluminum hydroxides, aluminum trihydroxide, boehmite, pseudo-boehmite, gibbsite, bayerite, transition aluminas, alpha-alumina, gamma-alumina, silica/alumina, silica, silicates, aluminates, calcium aluminate, barium hexaaluminate, calcined hydrotalcites, zeolites, zinc oxide, chromium oxides, magnesium oxides, zirconia oxides, or a mixture or combination thereof. Suitable heat-generating materials can be or can include those described in U.S. Pat. No. 9,725,380.

A selective hydrogen removal material can optionally be disposed within the reaction zone. In some embodiments, the selective hydrogen removal material can be configured to selectively combust molecular hydrogen produced during contact of the hydrocarbon-containing feed and the catalyst. Such material can also be referred to as a selective hydrogen combustion material. During the reaction, the selective hydrogen combustion material can selectively combust molecular hydrogen produced within the reaction zone, which can cause the selective hydrogen combustion material to lose lattice oxygen. During regeneration when the oxidant is introduced into the reaction zone, the selective hydrogen combustion material can be replenished with oxygen. In some embodiments, suitable selective hydrogen combustion material can be or can include, but is not limited to, one or more metal oxides with multiple redox states. In some embodiments, the metal oxide can be supported on one or more carriers. In some embodiments, the selective hydrogen combustion material can also include one or more promoters.

In some embodiments, the selective hydrogen combustion material can be or can include, but is not limited to, a metal in oxide form supported on a carrier, where the metal comprises an alkali metal, an alkaline earth metal, copper, chromium, molybdenum, vanadium, cerium, yttrium, scandium, tungsten, manganese, iron, cobalt, nickel, silver, bismuth, or a mixture or combination thereof. In some embodiments, the carrier can be or can include, but is not limited to, aluminum oxides, aluminum hydroxides, aluminum trihydroxide, boehmite, pseudo-boehmite, gibbsite, bayerite, transition aluminas, alpha-alumina, gamma-alumina, silica/alumina, silica, silicates, aluminates, calcium aluminate, barium hexaluminate, calcined hydrotalcites, zeolites, zinc oxide, chromium oxides, magnesium oxides, zirconia oxides, or a mixture or combination thereof. In some embodiments, the promoter can be or can include, but is not limited to, one or more alkali metal oxides or salts thereof, one or more alkaline earth metal oxides or salts thereof, or a mixture or combination thereof. In some embodiments, suitable alkali metal oxides or salts thereof and alkaline earth metal oxides or salts thereof can be or can include, but are not limited to, LiCl, NaCl, $Na_2O$, $K_2O$, KCl, $Na_2WO_4$, $K_2WO_4$, $Na_2MoO_4$, $Na_2MoO_4$, MgO, MgCl, or a mixture or combination thereof. In some embodiments, the selective hydrogen combustion material can be or can include, but is not limited to, the materials disclosed in U.S. Patent Application Publication No. 2016/0318828. In other embodiments, the selective hydrogen combustion material can be or can include, but is not limited to, one or more perovskite materials.

In some embodiments, the selective hydrogen removal material can be configured to selectively absorb molecular hydrogen produced during contact of the hydrocarbon-containing feed and the catalyst. Such material can also be referred to as a selective hydrogen absorption material. During the reaction, the selective hydrogen absorption material can selectively absorb molecular hydrogen produced within the reaction zone. The selective hydrogen absorption material can be regenerated by releasing the hydrogen from the selective hydrogen absorption material in subsequent steps. In some embodiments, the selective hydrogen absorption material can be or can include, but is not limited to, one or more metals such as such as Zr, Sc, Ti, Zr, V, Nb, Hf, Co, Mg, La, Pd, Ni, Fe, Cu, Ag, Cr, Th, or a mixture or combination thereof. In some embodiments, the selective hydrogen absorption material can be or can include, but is not limited to, the materials disclosed in U.S. Patent Application Publication No. 2015/0099914 and WO Publication No. WO 2016/187249.

In some embodiments, the catalyst can be intimately mixed with the heat-storing material, the heat-generating material, and/or the selective hydrogen removal material. In some embodiments, the active component of the catalyst and the active component of the heat-generating material and/or the active component of the selective hydrogen removal material can be intimately mixed and disposed on a same support. In other embodiments, the active component of the catalyst can be disposed on a catalyst support, followed by disposing the active component of the heat-generating material and/or the selective hydrogen removal material on the same catalyst support, or vice versa. In some embodiments, the catalyst support can be in powder or extrudate form. In other embodiments, the catalyst support can be in monolithic form.

In some embodiments, for fixed bed reactors, the catalyst and one or more of the heat-storing material, the heat-generating material, and the selective hydrogen removal material can be disposed within the reaction zone in a stacked bed fashion, i.e., stacked layers of catalyst and one or more of the optional heat-storing material, the heat-generating material, and the selective hydrogen removal material within the reaction zone. In other embodiments, the catalyst and one or more of the heat-storing material, the heat-generating material, and the selective hydrogen removal material can be disposed within the reaction zone in a staged reactor fashion, i.e., multiple reactors of alternating catalysts and one or more of the heat-storing material, the heat-generating material, and the selective hydrogen removal material, with the reactors connected in series. The reactors connected in series can be one of fixed bed reactor, fluidized bed reactor, reverse flow reactor, moving-bed reactor, etc.

In some embodiments, a hydrogen permeation membrane can be disposed within the reaction zone. The hydrogen permeation membrane can be configured to selectively remove molecular hydrogen from the first effluent within the reaction zone. For example, the hydrogen permeation membrane can be configured to allow hydrogen to flow therethrough while preventing or substantially preventing the flow of other molecules in the first effluent. In some embodiments, the hydrogen permeation membrane can be part of the reactor wall, as described in "Science, 2016, 353, 563" and "Journal of Membrane Science, 1993, 77, 221". In other embodiments, the hydrogen permeation membrane can be installed between reactors connected in series with the membrane configured to removes hydrogen from the effluent exiting the first reactor, before the effluent enters into the second reactor for further reaction. In some embodiments, the hydrogen permeation membrane can be or can include, but is not limited to, Pd-based membranes, zeolite-based membranes, or metal oxide-based membranes.

In some embodiments, hydrogen can be removed from the reaction zone by introducing an oxidant, e.g., molecular oxygen, into the reaction zone that can react with molecular hydrogen to produce $H_2O$. In some embodiments, the catalyst can serve as both a dehydrogenation catalyst and a hydrogen combustion catalyst. In other embodiments, another catalyst that serves solely as a hydrogen combustion catalyst can be disposed within the reaction zone. In some embodiments, suitable processes that can include introducing an oxidant into the reaction zone to remove molecular hydrogen therefrom can include those described in U.S. Pat. No. 7,678,956; and U.S. Patent Application Publication No. 2003/0139637.

In some embodiments, two or more reaction zones can be arranged in series so that the reaction zones that perform dehydrogenation, dehydroaromatization, and/or dehydrocyclization and the reaction zones that perform hydrogen combustion via oxidant addition are connected in an alternating fashion. In the reaction zones that perform the dehydrogenation, dehydroaromatization, and/or dehydrocyclization, no oxygen is introduced and the effluent therefrom is mixed with the oxidant in the reaction zones that that perform hydrogen combustion.

If the reaction zone includes any one or more of the heat-storing material, the heat-generating material, and the selective hydrogen removal material (collectively referred to as "the additional optional material"), the arrangement or distribution of the catalyst and the additional optional material with respect to one another is not critical. In some embodiments, however, it can be beneficial for of the catalyst and the additional optional material to be located proximate to one another, e.g., as an active material composite. In other embodiments, however, it can be beneficial for the catalyst and the additional optional material to be located separate from one another, e.g., in a first and a second layer or region within the reaction zone. In still other embodiments, it can be beneficial for the catalyst and the additional optional material to be relatively proximate, but not necessarily intimately combined or mixed as in an active material composite. For example, the catalyst and the additional optional material can be arranged in alternating beds or layers with respect to one another. Suitable active material composites arrangements or configurations can be prepared via well-known processes such as those disclosed in U.S. Patent Application Publication No. 2016/0318828.

Systems suitable for carrying out the processes disclosed herein can include systems that are well-known in the art such as the systems disclosed in WO Publication No. WO2017078894 and U.S. Patent Application Publication No. 2017/0121251.

Catalyst

The catalyst disposed within the reaction zone can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of the Group 8-10 element, based on the total weight of the support. In some embodiments, the catalyst can include ≤5.5 wt %, ≤4.5 wt %, ≤3.5 wt %, ≤2.5 wt %, ≤1.5 wt %, ≤1 wt %, ≤0.9 wt %, ≤0.8 wt %, ≤0.7 wt %, ≤0.6 wt %, ≤0.5 wt %, ≤0.4 wt %, ≤0.3 wt %, ≤0.2 wt %, ≤0.15 wt %, ≤0.1 wt %, ≤0.09 wt %, ≤0.08 wt %, ≤0.07 wt %, ≤0.06 wt %, ≤0.05 wt %, ≤0.04 wt %, ≤0.03 wt %, ≤0.02 wt %, ≤0.01 wt %, ≤0.009 wt %, ≤0.008 wt %, ≤0.007 wt %, ≤0.006 wt %, ≤0.005 wt %, ≤0.004 wt %, ≤0.003 wt %, or ≤0.002 of the Group 8-10 element, based on the total weight of the support. In some embodiments, the catalyst can include >0.001 wt %, >0.003 wt %, >0.005 wt %, >0.007 wt %, >0.009 wt %, >0.01 wt %, >0.02 wt %, >0.04 wt %, >0.06 wt %, >0.08 wt %, >0.1 wt %, >0.13 wt %, >0.15 wt %, >0.17 wt %, >0.2 wt %, >0.2 wt %, >0.23, >0.25 wt %, >0.27 wt %, or >0.3 wt % and <0.5 wt %, <1 wt %, <2 wt %, <3 wt %, <4 wt %, <5 wt %, or <6 wt % of the Group 8-10 element based on the total weight of the support. In other embodiments, the first catalyst, the second catalyst, and any intermediate catalyst(s) can each include >0.025 wt %, >0.05 wt %, >0.1 wt %, >0.13 wt %, >0.15 wt %, >0.17 wt %, >0.2 wt %, >0.2 wt %, >0.23, >0.25 wt %, >0.27 wt %, or >0.3 wt % and <0.5 wt %, <1 wt %, <2 wt %, <3 wt %, <4 wt %, <5 wt %, or <6 wt % of the Group 8-10 element based on the total weight of the support.

In some embodiments, the Group 8-10 element can be or can include, but is not limited to, Fe, Co, Ni, Ru, Pd, Os, Ir, Pt, a combination thereof, or a mixture thereof. In at least one embodiment, the Group 8-10 element can be or can include Pt. If two or more Group 8-10 elements are disposed on the support, the first catalyst, the second catalyst, and any intermediate catalyst(s) can each include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of a combined amount of the two or more Group 8-10 elements disposed on the support, based on the weight of the total weight of the support. The support in the catalyst can be or can include, but is not limited to, one or more elements having an atomic number of 4, 12, 20-22, 30, 38-40, 48, or 56-71. Said another way, the support in the catalyst can be or can include one or more Group 2 elements, one or more Group 4 elements, one or more Group 12 elements, one or more elements having an atomic number of 21, 39, or 57-71, combinations thereof, or mixture thereof. In some embodiments, the Group 2 element, the Group 4 element, the Group 12 element, and/or the element having an atomic number of 21, 39, or 57-71 can be present in its elemental form. In other embodiments, the Group 2 element, the Group 4 element, the Group 12 element, and/or the element having an atomic number of 21, 39, or 57-71 can be present in the form of a compound. For example, the Group 2 element, the Group 4 element, the Group 12 element, and/or the element having an atomic number of 21, 39, or 57-71 can be present as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, a mixture of any two or more compounds that include the Group 2 element, the Group 4 element, the Group 12 element, and/or the element having an atomic number of 21, 39, or 57-71 can be present in different forms. For example, a first compound can be an oxide and a second compound can be an aluminate where the first compound and the second compound include the same or different Group 2 element, Group 4 element, Group 12 element, and/or element having an atomic number of 21, 39, or 57-71, with respect to one another.

In some embodiments, the support in the catalyst can be or can include at least one of: w wt % of the one or more Group 2 elements, x wt % of the one or more Group 4 elements, y wt % of the one or more Group 12 elements, and z wt % of the one or more elements having an atomic number of 21, 39, or 57-71 based on the weight of the support, where w, x, y, and z are independently in a range from 0 to 100, and where w+x+y+z is ≤100. Any Group 2 element present in the support in the catalyst can be associated with a wt % m based on the weight of the support, any Group 4 element present in the support in the catalyst can be associated with a wt % n based on the weight of the support, any Group 12 element present in the support in the catalyst can be associated with a wt % p based on the weight of the support, and any element having an atomic number of 21, 39, or 57-71 present in the support in the catalyst can be associated with a wt % q based on the weight of the support, where m, n, p, and q can independently be a number that is in a range from 1 to 100. In some embodiments, m, n, p, and q can each be equal to 1, 2, 15, or 30, or m can be equal to 1, n can be equal to 15, p can be equal to 15, and q can be equal to 1.

As used herein, "m" represents the minimum wt % of all Group 2 elements in the support, if none of the Group 4 elements, none of the Group 12 elements, and none of the elements having an atomic number of 21, 39, or 57-71 are present in the support. Similarly, as used herein, "n" represents the minimum wt % of all Group 4 elements in the support, if none of the Group 2 elements, none of the Group 12 elements, and none of the elements having an atomic number of 21, 39, or 57-71 are present in the support. Similarly, "p" represents the minimum wt % of all Group 12 elements in the support, if none of the Group 2 elements, none of the Group 4 elements, and none of the elements having an atomic number of 21, 39, or 57-71 are present in the support, Finally, "q" represents the minimum wt % of all elements having an atomic number of 21, 39, or 57-71 that are present in the support, if none of the Group 2 elements, none of the Group 4 elements, and none of the Group 12 elements are present in the support.

In some embodiments, a sum of w/m+x/n+y/p+z/q can be at least 1, based on the weight of the support in the catalyst. In other embodiments, a sum of w/m+x/n+y/p+z/q can be at least 1, at least 2, at least 4, at least 6, at least 8, at least 12, at least 24, at least 48, or at least 60, based on the weight of the support in the catalyst. In other embodiments, a sum of w/m+x/n+y/p+z/q can be in a range from 1, 2, 3, 4, 5, 6, 7, or 8 to 10, 12, 16, 24, 30, 48, or 60. In other embodiments, a sum of w/m+x/n+y/p+z/q can be in a range from 1 to 2, 2 to 4, 4 to 6, 6 to 8, 8 to 12, 12 to 24, 24 to 48, or 48 to 60.

As such, the m, n, p, and q not only specify the minimum amount of each group of elements present in the support when the other groups of elements are not present in the support, but also specify the minimum amount of each group of elements in the support when any one or more of the other groups of elements are also present in the support, which is explained by the following Example.

In this Example: m=4, n=8, p=12, q=20. If none of the Group 4 elements, none of the Group 12 elements, and none of the elements having an atomic number of 21, 39, or 57-71 are present in the support, then the total amount of any Group 2 element(s) in the support has to be >4 wt %, i.e., w/m≥1. If none of the Group 2 elements, none of the Group 12 elements, and none of the elements having an atomic number of 21, 39, or 57-71 are present in the support, then the total amount of any Group 4 element(s) present in the support has to be ≥8 wt %, i.e., x/n≥1. If none of the Group 2 elements, none of the Group 4 elements, and none of the elements having an atomic number of 21, 39, or 57-71 are present in the support, then the total amount of any Group 12 element(s) present in the support has to be ≥12 wt %, i.e., y/p≥1. If none of the Group 2 elements, none of the Group 4 elements, and none of the Group 12 elements exist on the support, then the total amount of any element(s) having an atomic number of 21, 39, or 57-71 present in the support has to be ≥20 wt %, i.e., z/q≥1.

If both Group 2 and 4 elements are present in the support and none of the Group 12 elements and none of the elements having an atomic number of 21, 39, or 57-71 are present in the support, then there is no need for the total amount of Group 2 element(s) to be ≥4 wt % since the Group 4 element(s) on the support share the role of the Group 2 element(s). Similarly, there is no need for the total amount of Group 4 element(s) to be ≥8 wt % since the Group 2 element(s) on the support share the role of the Group 4 element(s). Such an interchangeable relationship between the Group 2 and 4 elements is defined by m and n. Since m=4 and n=8, two mass units of the Group 4 element(s) interchanges one mass unit of the Group 2 element(s). For example, if the total amount of the Group 2 element(s) is w=1.1 wt % and the total amount of the Group 4 element(s) is x=4.3 wt %, then w/m+x/n=1.1/4+4.3/8=0.8125, which is ≤1, i.e., the total amount of the Group 2 and 4 elements is too little for the support to satisfy w/m+x/n+y/p+z/q is ≥1. In another example, if the total amount of the Group 2 element(s) is w=2.4 wt % and the total amount of the Group 4 element(s) is x=4.3 wt %, then w/m+x/n=2.4/4+4.3/8=1.1375, which is ≥1, such that the total amount of the Group 2 and Group 4 elements is sufficient to satisfy w/m+x/n+y/p+z/q is ≥1, despite that both w and x (2.4 and 4.3) are less than m and n (4 and 8), respectively.

The same principle also applies to cases when the support includes at least one element from three of the group of elements, e.g., Group 2, Group 4, and Group 12, as well as when the support includes each group of elements, i.e., at least one Group 2 element, at least one Group 4 element, at least one Group 12 element, and at least one element having an atomic number of 21, 39, or 57-71. For example, if the support includes 0.5 wt % of Mg (Group 2 element), 2 wt % of Ca (Group 2 element), 4 wt % of Ce (atomic number of 58), 3 wt % of Zr (Group 4 element), and 6 wt % of Zn (Group 12 element), then the equation would be: (0.5+2)/4+4/20+3/8+6/12=1.7, which is ≥1. In summary, m, n, p, and q is the minimum amount of each Group of elements in the support when the other Groups of elements are not present in the support. The equation w/m+x/n+y/p+z/q≥1 defines how the 4 groups of elements can work together in the support In some embodiments, m can be one of ten values selected from: 2, 4, 6, 8, 10, 12, 14, 16, 18, and 20; n can be one of twelve values selected from: 2, 4, 6, 8, 10, 12, 14, 16, 18, 20, 22, and 24; p can be one of twelve values selected from: 2, 4, 6, 8, 10, 12, 14, 16, 18, 20, 22, and 24; and q can be one of twelve values selected from: 2, 4, 6, 10, 14, 18, 22, 26, 30, 34, 38, and 40, where m, n, p, and q can be any combination such that there are 17,280 (10×12×12×12) distinct combinations. In other embodiments, m can be equal to 2, 7, 10, or 20, n can be 2, 10, 20, or 25, p can be 2, 10, 20, or 25, and q can be 2, 10, 30, or 40, where m, n, p, and q can be any combination such that there are 256 (4×4×4×4) distinct combinations. In some embodiments, m, n, p, and q can each be equal to 2, 10, 15, or 30. In other embodiments, m can be equal to 7, n can be equal to 10, p can be equal to 10, and q can be equal to 10. In other embodiments, m can be equal to 7, n can be equal to 20, p can be equal to 20, and q can be equal to 10. In other embodiments, m can be equal to 10, n can be equal to 20, p can be equal to 20, and q can be equal to 30. In other embodiments, m can be equal to 7, n can be equal to 10, p can be equal to 10, and q can be equal to 30.

In some embodiments, w, x, y, and z can independently be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100, where a sum of w, x, y, z is ≤100.

In some embodiments, when the support in the catalyst includes the Group 2 element, a molar ratio of the Group 2 element to the Group 8-10 element can be in a range from 0.24, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, 9,500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000, 300,000, 400,000, 500,000, 600,000, 700,000, 800,000, or 900,000. In some embodiments, when the support in catalyst includes the Group 4 element, a molar ratio of the Group 4 element to the Group 8-10 element can be in a range from 0.18, 0.3, 0.5, 1, 10, 50, 100, 200, 300, 400, 500, 600, 700, 810, 1,000, or 5,000 to 10,000, 20,000, 30,000, 40,000, 50,000, 60,000, 70,000, or 81,000. In some embodiments, when the support in the catalyst includes the Group 12 element, a molar ratio of the Group 12 element to the Group 8-10 element can be in a range from 0.29, 0.5, 1, 10, 50, or 100 to 200, 300, 400, 500, 590, 600, or 1,000 to 5,000, 10,000, 20,000, 30,000, 40,000, 50,000 or 59,000. In some embodiments, when the support in the catalyst includes the element having an atomic number of 21, 39, or 57-71, a molar ratio of the element having an atomic number of 21, 39, or 57-71 to the Group 8-10 element can be in a range from 0.19, 0.5, 1, 10, 50, 100, or 150 to 200, 250, 300, 350, 400, 438, 500, 750, or 1,000 to 5,000, 10,000, 20,000, 30,000, 40,000, or 43,800. In some embodiments, when the support in the catalyst includes two or more of the Group 2, 4, or 12 element and the element having an atomic number of 21, 39, or 57-71, a molar ratio of a combined amount of any Group 2 element, any Group 4 element, any Group 12 element, and any element having an atomic number of 21, 39, or 57-71 to the Group 8-10 element can be in a range from 0.18, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, 9,500, 10,000, 15,000, 20,000, 25,000, 30,000, 35,000, 40,000, 43,800, 45,000, 50,000, 55,000, 59,000, 60,000, 65,000, 70,000, 75,000, 80,000, 81,000, 85,000, 90,000, 95,000, 100,000, 200,000, 300,000, 400,000, 500, 000, 600,000, 700,000, 800,000, or 900,000.

In some embodiments, the support in the catalyst can be or can include, but is not limited to, one or more of the following compounds: $Mg_uZn_{1-u}O$, where u is a positive number; $Zn_vAl2O3_{+v}$, where v is a positive number; $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number. BeO; MgO; CaO; BaO; SrO; $BeCO_3$; $MgCO_3$; $CaCO_3$; $SrCO_3$, $BaCO_3$; $ZrO_2$; ZrC; ZrN; $ZrSiO_4$; $CaZrO_3$; $Ca_7ZrAl_6O_{18}$; $TiO_2$; TiC; TiN; $TiSiO_4$; $CaTiO_3$; $Ca_7Al_6O_{18}$; $HfO_2$; HfC; HfN; $HfSiO_4$; $HfZrO_3$; $Ca_7HfAl_6O_{18}$; ZnO; $Zn_3(PO_4)_2$; $Zn(ClO_3)_2$; $ZnSO_4$; $B_2O_6Zn_3$; $Zn_3N_2$; $ZnCO_3$; $CeO_2$; $Y_2O_3$; $La_2O_3$; $Sc_2O_3$; $Pr_6O_{11}$; $CePO_4$; $CeZrO_4$; $CeAlO_3$; $BaCeO_3$; $CePO_4$; Yttria-stabilized $ZrO_2$; one or more magnesium chromates, one or more magnesium tungstates, one or more magnesium molybdates combinations thereof, and mixtures thereof.

The $Mg_uZn_{1-u}O$, where u is a positive number, if present as the support or as a component of the support in the catalyst can have a molar ratio of Mg to Zn in a range from 1, 2, 3, or 6 to 12, 25, 50, or 100. The $ZnvAl2O3_{+v}$, where v is a positive number, if present as the support or as a component of the support in the catalyst can have a molar ratio of Zn to Al in a range from 0.05, 0.3, or 0.6 to 0.9, 1.5, or 3 The $Mg_wAl_2O_{3+w}$, where w is a positive number, if present as the support or as a component of the support in the catalyst can have a molar ratio of Mg to Al in a range from 1, 2, 3, 4, or 5 to 6, 7, 8, 9, or 10. The $Ca_xAl_2O_{3+x}$, where x is a positive number, if present as the support or as a component of the support in the catalyst can have a molar ratio of Ca to Al in a range from 1:12, 1:4, 1:2, 2:3, 5:6, 1:1, 12:14, or 1.5:1. In some embodiments, the $Ca_xAl_2O_{3+x}$ can include tricalcium aluminate, dodecacalcium hepta-aluminate, moncalcium aluminate, moncalcium dialuminate, monocalcium hexa-aluminate, dicalcium aluminate, pentacalcium trialuminate, tetracalcium trialuminate, or any mixture thereof. The $Sr_yAl_2O_{3+y}$, where y is a positive number, if present as the support or as a component of the support in the catalyst can have a molar ratio of Sr to Al in a range from 0.05, 0.3, or 0.6 to 0.9, 1.5, or 3. The $Ba_zAl_2O_{3+z}$, where z is a positive number, if present as the support or as a component of the support in the catalyst can have a molar ratio of Ba to Al 0.05, 0.3, or 0.6 to 0.9, 1.5, or 3.

In some embodiments, the support in the catalyst can also include, but is not limited to, at least one metal element and/or at least one metalloid element selected from Groups 5, 6, 7, 11, 13, 14, 15, and 16 and/or at least one compound thereof. If the support in the catalyst also includes a compound that includes the metal element and/or metalloid element selected from Groups 5, 6, 7, 11, 13, 14, 15, and 16, the compound can be present in the support as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, suitable compounds that include the metal element and/or metalloid element selected from Groups 5, 6, 7, 11, 13, 14, 15, and 16 can be or can include, but are not limited to, one or more of the following: $B_2O_3$, $AlBO_3$, $Al_2O_3$, $SiO_2$, SiC, $Si_3N_4$, an aluminosilicate, VO, $V_2O_3$, $VO_2$, $V_2O_5$, $Ga_2O_3$, $In_2O_3$, $Mn_2O_3$, $Mn_3O_4$, MnO, one or more molybdenum oxides, one or more tungsten oxides, one or more zeolites, and mixtures and combinations thereof.

In some embodiments, the support can include the Group 2 element and Al and can be in the form of a mixed Group 2 element/Al metal oxide that has O, Mg, and Al atoms mixed on an atomic scale. In some embodiments the support can be or can include the Group 2 element and Al in the form of an oxide or one or more oxides of the Group 2 element and $Al_2O_3$ that can be mixed on a nm scale. In some embodiments, the support can be or can include an oxide of the Group 2 element, e.g., MgO, and $Al_2O_3$ mixed on a nm scale. In some embodiments, the support can be produced by calcining hydrotalcite.

In some embodiments, the support can be or can include a first quantity of the Group 2 element and Al in the form of a mixed Group 2 element/Al metal oxide and a second quantity of the Group 2 element in the form of an oxide of the Group 2 element. In such embodiment, the mixed Group 2 element/Al metal oxide and the oxide of the Group 2 element can be mixed on the nm scale and the Group 2 element and Al in the mixed Group 2 element/Al metal oxide can be mixed on the atomic scale.

In other embodiments, the support can be or can include a first quantity of the Group 2 element and a first quantity of Al in the form of a mixed Group 2 element/Al metal oxide, a second quantity of the Group 2 element in the form of an oxide of the Group 2 element, and a second quantity of Al in the form of $Al_2O_3$. In such embodiment, the mixed Group 2 element/Al metal oxide, the oxide of the Group 2 element, and the $Al_2O_3$ can be mixed on a nm scale and the Group 2 element and Al in the mixed Group 2 element/Al metal oxide can be mixed on the atomic scale.

In some embodiments, when the support includes the Group 2 element and Al, a weight ratio of the Group 2 element to the Al in the support can be in a range from 0.001, 0.005, 0.01, 0.05, 0.1, 0.15, 0.2, 0.3, 0.5, 0.7, or 1 to 3, 6, 12.5, 25, 50, 75, 100, 200, 300, 400, 500, 600, 700, 800, 900, or 1,000. In some embodiments, when the support includes Al, the support can include Al in a range from 0.5 wt %, 1 wt %, 1.5 wt %, 2 wt %, 2.1 wt %, 2.3 wt %, 2.5 wt %, 2.7 wt %, 3 wt %, 4 wt %, 5 wt %, 6 wt %, 7 wt %, 8 wt %, 9 wt %, 10 wt %, or 11 wt % to 15 wt %, 20 wt %, 25 wt %, 30 wt %, 40 wt %, 45 wt %, or 50 wt %, based on the weight of the support.

In some embodiments, the support can include ≥3 wt %, ≥6 wt %, ≥11 wt %, ≥15 wt %, ≥20 wt %, ≥25 wt %, ≥, 30 wt %, or ≥ of a Group 2 element based on the weight of the support. In some embodiments, the Group 2 element can be or can include, but is not limited to, Mg. In some embodiments, the support can be or can include, but is not limited to, calcined hydrotalcite.

In some embodiments, the support in the catalyst can also include one or more promoters disposed thereon. The promoter can be or can include, but is not limited to, Sn, Ga, Zn, Ge, In, Re, Ag, Au, Cu, a combination thereof, or a mixture thereof. As such, the promoter if present as a component of the catalyst, can be present as a component of the support, as a promoter disposed on the support, or both as a component of the support and as a promoter disposed on the support. In some embodiments, the promoter can be associated with the Group 8-10 element, e.g., Pt. For example, the promoter and the Group 8-10 element disposed on the support in the catalyst can form Group-8-10 element-promoter clusters that can be dispersed on the support. The promoter, if present, can improve the selectivity/activity/longevity of the catalyst for a given upgraded hydrocarbon. In some embodiments, the addition of the promoter can improve the propylene selectivity of the catalyst when the hydrocarbon-containing feed includes propane. The catalyst can include the promoter in an amount of 0.01 wt %, 0.05 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 3 wt %, 5 wt %, 7 wt %, or 10 wt %, based on the weight of the support.

In some embodiments, the support in the catalyst can also include one or more alkali metal elements disposed on the support. The alkali metal element, if present, can be or can include, but is not limited to, Li, Na, K, Rb, Cs, a combination thereof, or a mixture thereof. In at least some embodiments, the alkali metal element ca be or can include K and/or Cs. The alkali metal element, if present, can improve the selectivity of the catalyst particles for a given upgraded hydrocarbon. The catalyst can include the alkali metal element in an amount 0.01 wt %, 0.05 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, or 5 wt %, based on the weight of the support.

Catalyst Preparation

The preparation of the support of the catalyst can be accomplished via any known process. For simplicity and ease of description, the preparation of a suitable support that includes a mixed oxide of magnesium and aluminum (Mg(Al)O or $MgO/Al_2O_3$) will be described in more detail. Catalyst synthesis techniques are well-known and the following description is for illustrative purposes and not to be considered as limiting the synthesis of the support or the catalyst. In some embodiments, to make the $MgO/Al_2O_3$ mixed oxide support, Mg and Al precursors such as $Mg(NO_3)_2$ and $Al(NO_3)_3$ can be mixed together, e.g., ball-milled, followed by calcination to produce the support. In another embodiment, the two precursors can be dissolved in $H_2O$, stirred until dry (with heat optionally applied), followed by calcination to produce the support. In another embodiment, the two precursors can be dissolved in $H_2O$, followed by the addition of a base and a carbonate, e.g., $NaOH/Na_2CO_3$ to produce hydrotalcite, followed by calcination to produce the support. In another embodiment, a commercial ready MgO and $Al_2O_3$ may be mixed and ball-milled. In another embodiment, the $Mg(NO_3)_2$ precursor can be dissolved in $H_2O$ and the solution can be impregnated onto an existing support, e.g., an $Al_2O_3$ support, that can be dried and calcined to produce the support. In another embodiment, Mg from $Mg(NO_3)_2$ can be loaded onto an existing $Al_2O_3$ support through ion adsorption, followed by liquid-solid separation, drying and calcination to produce the support. Without wishing to be bound by theory, it is believed that the inorganic support produced via any one of the above methods and/or other methods can include (i) the Mg and Al mixed together on the nm scale, (ii) the Mg and Al in the form of a mixed Mg/Al metal oxide, or (iii) a combination of (i) and (ii).

Group 8-10 metals and any promoter and/or any alkali metal element may be loaded onto the mixed oxide support by any known technique. For example, one or more Group 8-10 element precursors, e.g., chloroplatinic acid, tetramineplatinum(II) nitrate, and/or tetramineplatinum(II) hydroxide, one or more promoter precursors (if used), e.g., a salt such as $SnCl_4$ and/or $AgNO_3$, and one or more alkali metal element precursors (if used), e.g., $KNO_3$, KCl, and/or NaCl, can be dissolved in water. In some embodiments, the Group 8-10 element precursor can be or can include, but is not limited to, chloroplatinic acid hexahydrate, tetraammineplatinum(II) nitrate, platinum(II) oxalate, platinum(II) acetylacetonate, platinum(II) bromide, platinum(II) iodide, platinum(II) chloride, platinum(IV) chloride, platinum(II) diammine dichloride, ammonium tetrachloroplatinate(II), tetraammineplatinum(II) chloride hydrate, tetraammineplatinum(II) hydroxide hydrate, iron nitrate, rhodium(III) nitrate, ruthenium(III) nitrate, cobalt(II) nitrate hexahydrate, nickel(II) nitrate hexahydrate, palladium(II) nitrate dihydrate, or any mixture thereof. In some embodiments, the promoter precursor can be or can include, but is not limited to, tin(II) oxide, tin(IV) oxide, tin(IV) chloride pentahydrate, tin(II) chloride dihydrate, tin citrate, tin sulfate, tin oxalate, tin(II) bromide, tin(IV) bromide, tin(II) acetylacetonate, tin(II) acetate, tin(IV) acetate, silver(I) nitrate, gold(III) nitrate, copper(II) nitrate, gallium(III) nitrate, or any mixture thereof. In some embodiments, the alkali metal element precursor can be or can include, but is not limited to, lithium nitrate, sodium nitrate, potassium nitrate, rubidium nitrate, cesium nitrate, or any mixture thereof The solution can be impregnated onto the support, followed by drying and calcination to produce the catalyst. In some embodiments, the Group 8-10 element precursor and optionally the promoter precursor and/or the alkali metal element precursor can be loaded onto the support at the same time, or separately in a sequence separated by drying and/or calcination steps to produce the catalyst. In other embodiments, the Group 8-10 element and, optionally the promoter and/or alkali metal element, can be loaded onto the support by chemical vapor deposition, where the precursors are volatilized and deposited onto the support, followed by calcination to produce the catalyst. In other embodiments, the Group 8-10 element precursor and, optionally, the promoter precursor and/or alkali metal precursor, can be loaded onto the support through ion adsorption, followed by liquid-solid separation, drying and calcination to produce the catalyst. Optionally, the catalyst can also be synthesized using a one-pot synthesis method where the precursors of the support, Group 8-10 metal active phase and the promoters are all mixed together, dry or wet, with or without any other additives to aid the synthesis, followed by drying or spray drying and calcination to produce the catalyst. In some embodiments, the drying or calcination may be carried out in an oxidative environment, or a reductive environment, or an inert environment, or a combination of two or more of the environments. In some embodiments, a suitable oxidative environment can be provided by air, enriched air, $O_2$, $O_2$ diluted by one or more inert gases, $O_3$, $O_3$ diluted by one or more inert gases, or any mixture thereof. In some embodiments, a suitable reductive environment can be provided by $H_2$, CO, syngas, or any reductive gas diluted by one or more inert gases. In some embodiments, a suitable inert environment can be provided by steam, $N_2$, Ar, He, or any mixture of the above. While drying/calcination is typically accompanied by the release of one or more volatiles, in some embodiments, the drying/calcination step can be preceded by an equilibration step where no release of volatiles is expected.

The as-synthesized catalyst, when examined under scanning electron microscope or transmission electron microscope, can appear as either primary particles, as agglomerates of primary particles, as aggregates of primary particles, or a combination thereof. Primary particles, agglomerates of primary particles and aggregates of primary particles are described in Powder Technology 181 (2008) 292-300. The primary particles in the as-synthesized catalyst, when examined under scanning electron microscope or transmission electron microscope, can have an average cross-sectional length or average particle size, e.g., a diameter when spherical, in a range from 0.2 nm, 0.5 nm, 1 nm, 5 nm, 10 nm, 25 nm, 30 nm, 40 nm 50 nm, 60 nm, 70 nm, 80 nm, 90 nm, 100 nm, 150 nm, 200 nm, 250 nm, 300 nm, 350 nm, 400 nm, 450 nm, or 500 nm to 1 µm, 10 µm, 25 µm, 50 µm, 100 µm, 150 µm, 200 µm, 250 µm, 300 µm, 400 µm, or 500 µm. In some embodiments, the primary particles in the as-synthesized catalyst can have an average particle size of 0.2 nm to 500 µm, 0.5 nm to 300 µm, 1 nm to 200 µm, 2 nm to 100 µm, 2 nm to 500 nm, or 2 nm to 100 nm, as measured by a transmission electron microscope.

The as-synthesized catalyst can have a surface area in a range from 0.1 m$^2$/g, 1 m$^2$/g, 10 m$^2$/g, or 100 m$^2$/g to 500 m$^2$/g, 800 m$^2$/g, 1,000 m$^2$/g, or 1,500 m$^2$/g. The surface area of the catalyst can be measured according to the Brunauer-Emmett-Teller (BET) method using adsorption-desorption of nitrogen (temperature of liquid nitrogen, 77 K) with a Micromeritics 3flex instrument after degassing of the powders for 4 hours at 350° C. More information regarding the method can be found, for example, in "Characterization of Porous Solids and Powders: Surface Area, Pore Size and Density," S. Lowell et al., Springer, 2004.

In some embodiments, the support can be extruded or otherwise formed into any desired monolithic structure and the Group 8-10 element and any optional promoter and/or alkali metal element can be disposed thereon. Suitable monolithic structures can be or can include, but are not limited to, structures having a plurality of substantially parallel internal passages such as those in the form of a ceramic honeycomb. In some embodiments, the support can be in the form of beads, spheres, rings, toroidal shapes, irregular shapes, rods, cylinders, flakes, films, cubes, polygonal geometric shapes, sheets, fibers, coils, helices, meshes, sintered porous masses, granules, pellets, tablets, powders, particulates, extrudates, cloth or web form materials, honeycomb matrix monolith, including in comminuted or crushed forms, and the Group 8-10 element and any optional promoter and/or alkali metal element can be disposed thereon.

The as-synthesized catalyst can be formulated into one or more appropriate forms for different hydrocarbon upgrading processes. Alternatively, the support of in the catalyst can be formulated into appropriate forms for different hydrocarbon upgrading processes, before the addition of the Group 8-10 element and, any optional promoter and/or alkali metal element. During formulation, one or more binders and/or additives can be added to the catalyst and/or the support to improve the chemical/physical properties of the catalyst ultimately produced and used in the process. The binder/additives can be or can include, but are not limited to, silica, silica sol, silica-alumina, alumina, aluminum chlorhydrol, peptized alumina, aluminosilicates, smectites, kaolins, acid-treated metakaolins, illites, chlorites, attapulgites, pillared interlayered clays and mixed layer clays, silanes, alkoxysilanes, aryloxysilanes, acyloxysilanes, oximinosilanes, halosilanes, aminoxysilanes, aminosilanes, amidosilanes, silazanes, silicones, or a mixture thereof.

In some embodiments, the catalyst can be formulated via the well-known spray drying process to produce spray dried catalyst particles. Spray-dried catalyst particles having an average cross-sectional area in a range from 20 µm, 40 µm, or 50 µm to 80 µm, 90 µm, or 100 µm are typically used in an FCC type fluid-bed reactor. To make spray-dried catalyst particles, the support, the Group 8-10 element, and any additional components, e.g., the promoter and/or the alkali metal, can be made into a slurry with binder/additive in the slurry before spray-drying and calcination. Alternatively, the Group 8-10 element, and any additional components, e.g., the promoter and/or the alkali metal, can be added to the formulated support to produce the formulated catalyst.

Suitable processes that can be used to prepare the catalyst disclosed herein can include the processes described in U.S. Pat. Nos. 4,788,371; 4,962,265; 5,922,925; 8,653,317; EP Patent No. EP0098622; Journal of Catalysis 94 (1985), pp. 547-557; and/or Applied Catalysis 54 (1989), pp. 79-90.

In some embodiments, the formulated catalyst can have a particle density in a range from 0.5 g/cm$^3$, 0.7 g/cm$^3$, 0.9 g/cm$^3$, 1 g/cm$^3$, 1.2 g/cm$^3$, or 1.3 g/cm$^3$, to 1.5 g/cm$^3$, 1.8 g/cm$^3$, 2 g/cm$^3$, 2.3 g/cm$^3$, 2.5 g/cm$^3$, 2.7 g/cm$^3$, or 3 g/cm$^3$. The "particle density" refers to the density of the catalyst particles including the pore volume in g/cm$^3$ and can be measured by mercury porosimetry. The particle density of the catalyst particles can be measured according to UOP578-11. In some embodiments, the catalyst particles can have an average particle size and particle density consistent with a Geldart A definition.

When the process includes two or more reaction zones, the composition of the catalyst disposed within each reaction zone can be the same or different with respect to one another. In some embodiments, the composition of a catalyst disposed in a first reaction zone can be the same or substantially the same as the composition of a catalyst disposed in a second reaction zone. In other embodiments, the composition of a catalyst disposed in a first reaction zone can be different that the composition of a catalyst disposed in a second reaction zone. The catalysts disposed in different reaction zones can have a composition according to the catalyst compositions described here. In some embodiments, a first hydrocarbon-containing feed, e.g., propane, can be introduced into a first reaction zone and a second hydrocarbon-containing feed, e.g., isobutane, can be introduced into a second reaction zone and the composition of the first catalyst can be different than the composition of the second catalyst to produce the desired upgraded hydrocarbon, e.g., propylene in the first reaction zone and isobutylene in the second reaction zone.

Hydrocarbon-Containing Feed

The $C_2$-$C_{16}$ alkanes can be or can include, but are not limited to, ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, or a mixture thereof. For example, the hydrocarbon-containing feed can include propane, which can be dehydrogenated to produce propylene, and/or isobutane, which can be dehydrogenated to produce isobutylene. In another example, the hydrocarbon-containing feed can include liquid petroleum gas (LP gas), which can be in the gaseous phase when contacted with the catalyst particles. In some embodiments, the hydrocarbon in the hydrocarbon-containing feed can be composed of substantially a single alkane such as propane. In some embodiments, the hydrocarbon-containing feed can include ≥50 mol %, ≥75 mol %, ≥95 mol %, ≥98 mol %, or ≥99 mol % of a single $C_2$-$C_{16}$ alkane, e.g., propane, based on a total weight of all hydrocarbons in the hydrocarbon-containing feed. In some embodiments, the hydrocarbon-containing feed can include at least 50 vol %, at least 55 vol %, at least 60 vol %, at least 65 vol %, at least 70 vol %, at least 75 vol %, at least 80 vol %, at least 85 vol %, at least 90 vol %, at least 95 vol %, at least 97 vol %, or at least 99 vol % of a single $C_2$-$C_{16}$ alkane, e.g., propane, based on a total volume of the hydrocarbon-containing feed.

The $C_8$-$C_{16}$ alkyl aromatic hydrocarbons can be or can include, but are not limited to, ethylbenzene, propylbenzene, butylbenzene, one or more ethyl toluenes, or a mixture thereof. In some embodiments, the hydrocarbon-containing feed can include ≥50 mol %, ≥75 mol %, ≥95 mol %, ≥98 mol %, or ≥99 mol % of a single $C_8$-$C_{16}$ alkyl aromatic, e.g., ethylbenzene, based on a total weight of all hydrocarbons in the hydrocarbon-containing feed. In some embodiments, the ethylbenzene can be dehydrogenated to produce styrene. As such, in some embodiments, the processes disclosed herein can include propane dehydrogenation, butane dehydrogenation, isobutane dehydrogenation, pentane dehydrogenation, pentane dehydrocyclization to cyclopentadiene, naphtha reforming, ethylbenzene dehydrogenation, ethyltoluene dehydrogenation, and the like.

In some embodiments, the hydrocarbon-containing feed can be diluted with one or more diluent gases. Suitable diluents can be or can include, but are not limited to, argon, neon, helium, molecular nitrogen, carbon dioxide, methane, molecular hydrogen, or a mixture thereof. If the hydrocarbon containing-feed includes a diluent, the hydrocarbon-containing feed can include 0.1 vol %, 0.5 vol %, 1 vol %, or 2 vol % to 3 vol %, 8 vol %, 16 vol %, or 32 vol % of the diluent, based on a total volume of any $C_2$-$C_{16}$ alkanes and any $C_8$-$C_{16}$ alkyl aromatic hydrocarbons in the hydrocarbon-containing feed. When the diluent includes molecular hydrogen, a molar ratio of the molecular hydrogen to a combined amount of any $C_2$-$C_{16}$ alkane and any $C_8$-$C_{16}$ alkyl aromatic hydrocarbons can be in a range from 0.1, 0.3, 0.5, 0.7, or 1 to 2, 3, 4, 5, 6, 7, 8, 9, or 10. In some embodiments, if the diluent is used, the diluent can be mixed with the hydrocarbon-containing feed and/or introduced or otherwise fed into the conversion zone as a separate feed via one or more inlets dedicated to feeding the diluent into the conversion zone. Similarly, the hydrocarbon-containing feed can also be introduced into the conversion zone via one or more inlets dedicated to feeding the hydrocarbon-containing feed into the conversion zone.

In some embodiments, the hydrocarbon-containing feed can be substantially free of any steam, e.g., <0.1 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include steam. For example, the hydrocarbon-containing feed can include 0.1 vol %, 0.3 vol %, 0.5 vol %, 0.7 vol %, 1 vol %, 3 vol %, or 5 vol % to 10 vol %, 15 vol %, 20 vol %, 25 vol %, 30 vol %, 35 vol %, 40 vol %, 45 vol %, or 50 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include ≤50 vol %, ≤45 vol %, ≤40 vol %, ≤35 vol %, ≤30 vol %, ≤25 vol %, ≤20 vol %, or ≤15 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include at least 1 vol %, at least 3 vol %, at least 5 vol %, at least 10 vol %, at least 15 vol %, at least 20 vol %, at least 25 vol %, or at least 30 vol % of steam, based on a total volume of any $C_2$-$C_{16}$ alkanes and any $C_8$-$C_{16}$ alkyl aromatic hydrocarbons in the hydrocarbon-containing feed. Similar to the diluent, if steam is fed into the conversion zone, the steam can be fed into the conversion zone as a component of the hydrocarbon-containing feed or via one or more separate inlets dedicated to introducing the steam into the conversion zone.

In some embodiments, the hydrocarbon-containing feed can include sulfur. For example, the hydrocarbon-containing feed can include sulfur in a range from 0.5 ppm, 1 ppm, 5 ppm, 10 ppm, 20 ppm 30 ppm, 40 ppm, 50 ppm, 60 ppm, 70 ppm, or 80 ppm to 100 ppm, 150 ppm, 200 ppm, 300 ppm, 400 ppm, or 500 ppm. In other embodiments, the hydrocarbon-containing feed can include sulfur in a range from 1 ppm to 10 ppm, 10 ppm to 20 ppm, 20 ppm to 50 ppm, 50 ppm to 100 ppm, or 100 ppm to 500 ppm. The sulfur, if present in the hydrocarbon-containing feed, can be or can include, but is not limited to, $H_2S$, dimethyl disulfide, as one or more mercaptans, or any mixture thereof. In some embodiments, the sulfur can be introduced into the conversion zone as a separate feed, as a component of the diluent if used, and/or as a component of the steam if used.

The hydrocarbon-containing feed can be substantially free or free of molecular oxygen. In some embodiments, the hydrocarbon-containing feed can include ≤5 mol %, ≤3 mol %, or ≤1 mol % of molecular oxygen ($O_2$). It is believed that providing a hydrocarbon-containing feed substantially-free of molecular oxygen substantially prevents oxidative coupling reactions that would otherwise consume at least a portion of the alkane and/or the alkyl aromatic hydrocarbon in the hydrocarbon-containing feed.

Recovery and Use of the Upgraded Hydrocarbons

The upgraded hydrocarbon can include at least one upgraded hydrocarbon, e.g., an olefin, water, unreacted hydrocarbons, unreacted molecular hydrogen, etc. The upgraded hydrocarbon can be recovered or otherwise obtained via any convenient process, e.g., by one or more conventional processes. One such process can include cooling the effluent to condense at least a portion of any water and any heavy hydrocarbon that may be present, leaving the olefin and any unreacted alkane or alkyl aromatic primarily in the vapor phase. Olefin and unreacted alkane or alkyl aromatic hydrocarbons can then be removed from the reaction product in one or more separator drums. For example, one or more splitters can be used to separate the dehydrogenated product from the unreacted hydrocarbon-containing feed.

In some embodiments, a recovered olefin, e.g., propylene, can be used for producing polymer, e.g., recovered propylene can be polymerized to produce polymer having segments or units derived from the recovered propylene such as polypropylene, ethylene-propylene copolymer, etc. Recovered isobutene can be used, e.g., for producing one or more of: an oxygenate such as methyl tert-butyl ether, fuel additives such as diisobutene, synthetic elastomeric polymer such as butyl rubber, etc.

EXAMPLES

The foregoing discussion can be further described with reference to the following non-limiting examples.

The following process steps were performed on the catalysts used in most examples below. All experiments were carried out at ambient pressure, except for the few exceptions as noted in the examples below.

1. A gas that included 10 vol % of $O_2$ in He, or air was passed through the catalyst at a regeneration temperature ($T_{regen}$) for a certain period of time ($t_{regen}$) to regenerate the catalyst.
2. Without changing the flow of the gas, the temperature within the reactor was changed from $T_{regen}$ to a reduction temperature ($T_{red}$).
3. The system was flushed with He gas.
4. A gas that included 10 vol % $H_2$ in Ar was passed through the catalyst at the $T_{red}$ for a certain period of time ($t_{red}$).
5. The system was flushed with He gas.
6. The temperature within the reactor from was changed from $T_{re}$a to a reaction temperature ($T_{rxn}$) in the presence of the inert gas.

7. A hydrocarbon-containing feed that included 90 vol % of $C_3H_8$ in Ar or Kr or He at a flow rate ($F_{rxn}$) was passed through the catalyst at the $T_{rxn}$ for a certain period of time ($t_{rxn}$). In some examples, the hydrocarbon-containing feed was passed through a sparger immersed in deionized water kept at a temperature of $T_1$, and then through a reflux with a carefully controlled temperature of $T_2$ before it was introduced into the reactor and reached the catalyst. When the sparger was used, the hydrocarbon-containing feed included a certain amount of steam within the reactor, which is shown in the relevant tables below.

8. The system was flushed with He gas.

9. The gas that included 10 vol % of $O_2$ in He, or air was again passed through the catalyst at $T_{rxn}$, and the temperature within the reactor was changed from $T_{rxn}$ to $T_{regen}$.

In certain examples, the catalyst reduction step was not carried out and the following steps were performed.

1. The gas that included 10 vol % of $O_2$ in He or air was passed through the catalyst at the $T_{regen}$ for the $t_{regen}$.
2. Without changing the flow of the gas, the temperature within the reactor was changed from $T_{regen}$ to $T_{rxn}$.
3. The system was flushed with the inert gas (such as He).
4. The hydrocarbon-containing feed that included 90 vol % of $C_3H_8$ in Ar or Kr or He at a flow rate of $F_{rxn}$ was passed through the catalyst at the $T_{rxn}$ for the $t_{rxn}$. In some examples, the hydrocarbon-containing feed was passed through the sparger immersed in deionized water kept at the temperature of $T_1$, and then through a reflux with carefully controlled temperature of $T_2$ before it was introduced into the reactor and reached the catalyst.
5. The system was flushed with an inert gas (such as He).
6. The gas that included 10 vol % of $O_2$ in He or air was again passed through the catalyst at $T_{rxn}$, and the temperature within the reactor was changed from $T_{rxn}$ to $T_{regen}$.

An AGILENT® microGC 490 was used to measure the composition of the reactor effluent every 1 minute to 1.5 minutes. The concentration of each component in the reactor effluent was then used to calculate the $C_3H_6$ yield and selectivity. The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in the data tables below. For some experiments, repeated cycles were conducted to understand catalyst stability. The $C_3H_6$ yield as reported in these examples are based on carbon only.

In each example, a certain amount of the catalyst $M_{cat}$ was mixed with an appropriate amount of quartz/SiC diluent and loaded in a quartz reactor. The amount of diluent is determined so that the catalyst bed (catalyst+diluent) is largely isothermal during operation. The dead volume of the reactor was filled with quartz chips/rods.

When the reaction temperature ($T_{rxn}$) was >620° C., thermal cracking of propane/propylene became significant. Since thermal cracking of propane/propylene has a much higher selectivity to $C_1$ and $C_2$ hydrocarbons, the overall selectivity to $C_3H_6$ is reduced. The amount of thermal cracking within the reactor is related to how much quartz/SiC diluent was added into the reactor and how well the dead volume within the reactor was reduced by the packing materials. Therefore, depending on how the reactor is packed in different experiments, the performance varies. As such, the experimental results shown in different tables are not necessarily comparable to one another.

Examples 1-23, Catalyst 1

Catalyst 1: The catalyst used in Examples 1-23 (Exs. 1-23) was a Pt-based, Sn-containing catalyst supported on an Mg/Al mixed oxide support, crushed and sieved to 20-40 mesh particle size. Elemental analysis showed that the catalyst contained 0.48 wt % of Pt, 1.25 wt % of Sn, 67.93 wt % of Mg, and 29.23 wt % of Al, based on the total weight of the metal elements, with an Mg to Al molar ratio of about 2.58.

Figure 2:
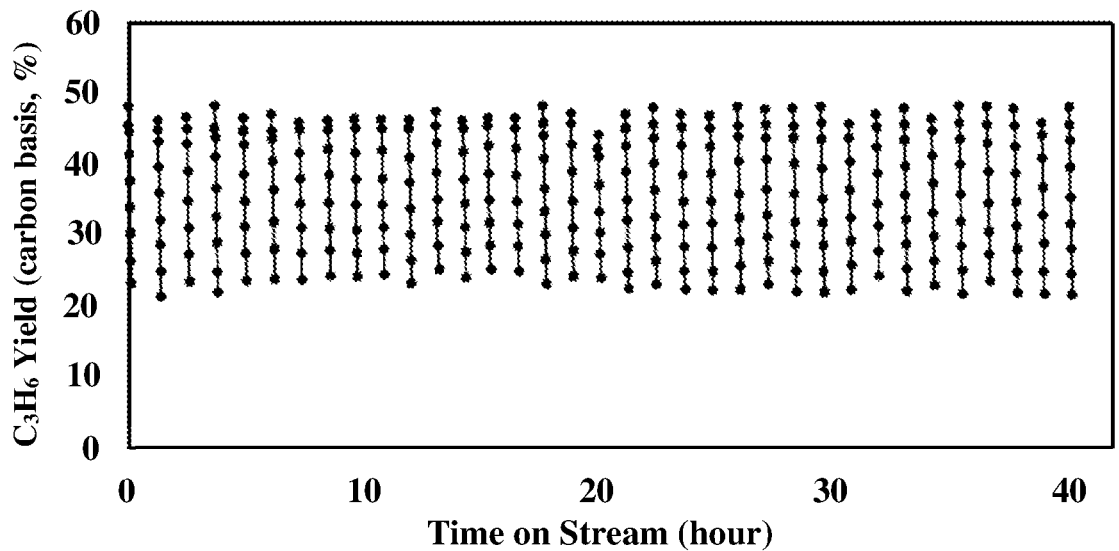
FIG. 2 shows the catalyst stability results of a catalyst used in Examples 1-3 after having undergone 35 cycles (regeneration, reduction, and dehydrogenation) carried out under the same conditions used in Example 1.

Table 1 shows the experimental results for Examples 1-3. A comparison between Ex. 1 and Ex. 3 shows that the reduction of the catalyst in the presence of molecular hydrogen after the oxidative regeneration improve the propylene yield. Ex. 1 and Ex. 3 also show that the catalyst is not very sensitive to the duration of the reduction step (1 minute vs. 5 minutes) under the experimental conditions used for these examples. At other conditions, however, there might be an optimal duration for the reduction step to be carried out. FIG. 2 shows the catalyst stability results of the catalyst used in Examples 1-3 after having undergone 35 cycles (regeneration, reduction, and dehydrogenation) carried out under the same conditions used in Example 1. Table 2 shows the experimental results for Examples 4 and 5. The results in Table 2 show that the reduction step can be carried out at different temperatures (670° C. versus 750° C.).

TABLE 1

|  |  | Ex. 1 | Ex. 2 | Ex. 3 |
|---|---|---|---|---|
| Catalyst |  | 1 | 1 | 1 |
| $M_{cat}$ (g) |  | 1 | 1 | 1 |
| $T_{rxn}$ (° C.) |  | 620 | 620 | 620 |
| $t_{rxn}$ (min) |  | 10 | 10 | 10 |
| $F_{rxn}$ (sccm) |  | 22 | 22 | 22 |
| $S_{vol}$ (%) |  | NA | NA | NA |
| $T_{red}$ (° C.) |  | 620 | NA | 620 |
| $t_{red}$ (min) |  | 1 | NA | 5 |
| $T_{regen}$ (° C.) |  | 620 | 620 | 620 |
| $t_{regen}$ (min) |  | 30 | 30 | 30 |
| Cycles |  | 35 | 1 | 1 |
| First cycle | $Y_{ini}$ | 48.1 | 21.2 | 48.2 |
|  | $Y_{end}$ | 23.2 | 6.8 | 24 |
|  | $S_{ini}$ | 98 | 96.4 | 98 |
|  | $S_{end}$ | 93.8 | 89.6 | 93.7 |

TABLE 2

|  |  | Ex. 4 | Ex. 5 |
|---|---|---|---|
| Catalyst |  | 1 | 1 |
| $M_{cat}$ (g) |  | 0.773 | 0.773 |
| $T_{rxn}$ (° C.) |  | 670 | 670 |
| $t_{rxn}$ (min) |  | 10 | 10 |
| $F_{rxn}$ (sccm) |  | 17 | 17 |
| $S_{vol}$ (vol %) |  | 11 | 11 |
| $T_{red}$ (° C.) |  | 670 | 750 |
| $t_{red}$ (min) |  | 1 | 1 |
| $T_{regen}$ (° C.) |  | 800 | 800 |
| $t_{regen}$ (min) |  | 30 | 30 |
| Cycles |  | 1 | 1 |
| First cycle | $Y_{ini}$ | 63.1 | 61.9 |
|  | $Y_{end}$ | 61.7 | 61 |
|  | $S_{ini}$ | 86.7 | 87.7 |
|  | $S_{end}$ | 87.9 | 88.3 |

Table 3 shows the experimental results for Examples 6-10. Examples 6-10 were conducted by introducing a partial plug at the exhaust of the reactor so that as the hydrocarbon-containing feed passed through the reactor at room temperature, e.g., 25° C., the pressure indicator upstream of the reactor read 1.43 bara. During the experiment, the gas volumetric flow rate in the reactor was expected to increase due to steam addition, higher T and volume expansion of the flow due to propane dehydrogenation. Therefore, the pressure within the reactor should have been significantly higher than 1.43 bara. Unfortunately, the pressure during reactor could not be monitored due to equipment limitations. Experiments 8-10 show the effect of conducting the regeneration at different temperatures and durations.

TABLE 3

|  |  | Ex. 6 | Ex. 7 | Ex. 8 | Ex. 9 | Ex. 10 |
|---|---|---|---|---|---|---|
| P (bara) | | 1.43 | 1.43 | 1.43 | 1.43 | 1.43 |
| Catalyst | | 1 | 1 | 1 | 1 | 1 |
| $M_{cat}$ (g) | | 0.773 | 0.773 | 0.773 | 0.773 | 0.773 |
| $T_{rxn}$ (° C.) | | 670 | 660 | 680 | 670 | 670 |
| $t_{rxn}$ (min) | | 10 | 10 | 10 | 10 | 10 |
| $F_{rxn}$ (sccm) | | 34 | 34 | 34 | 34 | 34 |
| $S_{vol}$ (vol %) | | 11 | 11 | 11 | 11 | 11 |
| $T_{red}$ (° C.) | | 670 | 660 | 680 | 670 | 670 |
| $t_{red}$ (min) | | 1 | 1 | 1 | 1 | 1 |
| $T_{regen}$ (° C.) | | 800 | 800 | 800 | 800 | 900 |
| $t_{regen}$ (min) | | 30 | 30 | 30 | 45 | 30 |
| Cycles | | 8 | 8 | 1 | 7 | 7 |
| First cycle | $Y_{ini}$ | 57.9 | 56.2 | 58.1 | 58.4 | 57.3 |
| | $Y_{end}$ | 55.9 | 53.9 | 55.2 | 56.7 | 54.1 |
| | $S_{ini}$ | 89 | 91 | 86.2 | 89 | 88.9 |
| | $S_{end}$ | 89.6 | 91.7 | 87 | 89.7 | 89.5 |
| Last cycle | $Y_{ini}$ | 57.5 | 56.2 | NA | 58.5 | NA |
| | $Y_{end}$ | 55.4 | 54.2 | NA | 57.1 | NA |
| | $S_{ini}$ | 88.9 | 91 | NA | 88.9 | NA |
| | $S_{end}$ | 89.7 | 91.7 | NA | 89.7 | NA |

Table 4 shows the experimental results for Examples 11-14. The result sin Table 4 shown the effect space velocity had on the performance of the catalyst. Table 5 shows the experimental results of Examples 15 and 16. Table 5 shows the effect of reduction in the presence of steam, respectively. Table 6 shows the results of Examples 17 and 18. Table 6 shows the effect of regeneration duration.

TABLE 4

|  |  | Ex. 11 | Ex. 12 | Ex. 13 | Ex. 14 |
|---|---|---|---|---|---|
| Catalyst | | 1 | 1 | 1 | 1 |
| $M_{cat}$ (g) | | 0.193 | 0.193 | 0.193 | 0.193 |
| $T_{rxn}$ (° C.) | | 670 | 670 | 670 | 700 |
| $t_{rxn}$ (min) | | 10 | 10 | 10 | 10 |
| $F_{rxn}$ (sccm) | | 34 | 17 | 9 | 17 |
| $S_{vol}$ (vol %) | | 11 | 11 | 11 | 11 |
| $T_{red}$ (° C.) | | 670 | 670 | 670 | 670 |
| $t_{red}$ (min) | | 1 | 1 | 1 | 1 |
| $T_{regen}$ (° C.) | | 800 | 800 | 800 | 800 |
| $t_{regen}$ (min) | | 30 | 30 | 30 | 30 |
| Cycles | | 1 | 1 | 1 | 1 |
| First cycle | $Y_{ini}$ | 54.1 | 59.3 | 60.6 | 58.5 |
| | $Y_{end}$ | 45 | 51.9 | 56 | 44.4 |
| | $S_{ini}$ | 95.2 | 92.8 | 89.6 | 86.3 |
| | $S_{end}$ | 94.4 | 92.3 | 89.3 | 82.8 |

TABLE 5

|  |  | Ex. 15 | Ex. 16 |
|---|---|---|---|
| Catalyst | | 1 | 1 |
| $M_{cat}$ (g) | | 0.193 | 0.193 |
| $T_{rxn}$ (° C.) | | 670 | 670 |
| $t_{rxn}$ (min) | | 10 | 10 |
| $F_{rxn}$ (sccm) | | 9 | 9 |
| $S_{vol}$ (vol %) | | 11 | 11 |
| $T_{red}$ (° C.) | | 670 | NA |
| $t_{red}$ (min) | | 1 | NA |
| $T_{regen}$ (° C.) | | 800 | 800 |
| $t_{regen}$ (min) | | 30 | 30 |
| Cycles | | 1 | 1 |
| First cycle | $Y_{ini}$ | 58.4 | 22.4 |
| | $Y_{end}$ | 50.2 | 13.7 |
| | $S_{ini}$ | 90.2 | 79.4 |
| | $S_{end}$ | 89.7 | 68.7 |

TABLE 6

|  |  | Ex. 17 | Ex. 18 |
|---|---|---|---|
| Catalyst | | 1 | 1 |
| $M_{cat}$ (g) | | 0.773 | 0.773 |
| $T_{rxn}$ (° C.) | | 670 | 670 |
| $t_{rxn}$ (min) | | 10 | 10 |
| $F_{rxn}$ (sccm) | | 17 | 17 |
| $S_{vol}$ (vol %) | | 11 | 11 |
| $T_{red}$ (° C.) | | 670 | 670 |
| $t_{red}$ (min) | | 1 | 1 |
| $T_{regen}$ (° C.) | | 800 | 800 |
| $t_{regen}$ (min) | | 30 | 10 |
| Cycles | | 1 | 1 |
| First cycle | $Y_{ini}$ | 58.2 | 56.7 |
| | $Y_{end}$ | 55.1 | 51.7 |
| | $S_{ini}$ | 89.5 | 89.7 |
| | $S_{end}$ | 89 | 89.1 |

Figure 3:
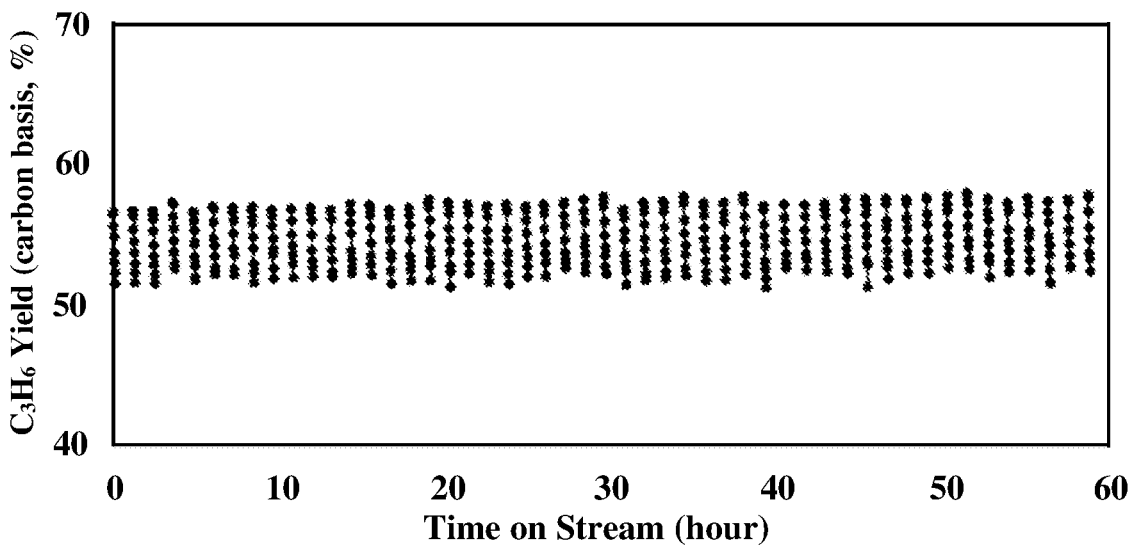
FIG. 3 shows the catalyst stability results of the catalyst used in Example 23 after having undergone 49 cycles (regeneration, reduction, and dehydrogenation) in the presence of steam.

Table 7 shows the results of Examples 19-22. Table 7 shows the effect the amount steam in the hydrocarbon-containing feed has on the yield and selectivity. In Ex. 23, the catalyst was subjected to 49 cycles total in the presence of about 11 vol % steam. The results of Ex. 23 are shown in Table 8. FIG. 3 shows the catalyst stability results of the catalyst used in Example 23 after having undergone 49 cycles (regeneration, reduction, and dehydrogenation) in the presence of steam.

Example 24, Catalyst 2

TABLE 7

|  |  | Ex. 19 | Ex. 20 | Ex. 21 | Ex. 22 |
|---|---|---|---|---|---|
| Catalyst | | 1 | 1 | 1 | 1 |
| $M_{cat}$ (g) | | 0.773 | 0.773 | 0.773 | 0.773 |
| $T_{rxn}$ (° C.) | | 670 | 670 | 650 | 650 |
| $t_{rxn}$ (min) | | 10 | 10 | 10 | 10 |
| $F_{rxn}$ (sccm) | | 17 | 17 | 17 | 17 |
| $S_{vol}$ (vol %) | | 3 | 11 | 11 | NA |
| $T_{red}$ (° C.) | | 670 | 670 | 650 | 650 |
| $t_{red}$ (min) | | 1 | 1 | 1 | 1 |
| $T_{regen}$ (° C.) | | 670 | 670 | 650 | 650 |
| $t_{regen}$ (min) | | 30 | 30 | 30 | 30 |
| Cycles | | 1 | 1 | 1 | 1 |
| First cycle | $Y_{ini}$ | 54.9 | 58.5 | 56.8 | 52.1 |
| | $Y_{end}$ | 49.9 | 55.4 | 55.3 | 22 |
| | $S_{ini}$ | 90.7 | 90.4 | 93.6 | 90.8 |
| | $S_{end}$ | 88.8 | 90 | 93.6 | 84.7 |

TABLE 8

|  |  | Ex. 23 |
|---|---|---|
| Catalyst |  | 1 |
| $M_{cat}$ (g) |  | 0.773 |
| $T_{rxn}$ (° C.) |  | 670 |
| $t_{rxn}$ (min) |  | 10 |
| $F_{rxn}$ (sccm) |  | 17 |
| $S_{vol}$ (vol %) |  | 11 |
| $T_{red}$ (° C.) |  | 670 |
| $t_{red}$ (min) |  | 1 |
| $T_{regen}$ (° C.) |  | 670 |
| $t_{regen}$ (min) |  | 30 |
| Cycles |  | 49 |
| First | $Y_{ini}$ | 56.5 |
| cycle | $Y_{end}$ | 51.6 |
|  | $S_{ini}$ | 89.8 |
|  | $S_{end}$ | 89 |
| Last | $Y_{ini}$ | 57.6 |
| cycle | $Y_{end}$ | 52.4 |
|  | $S_{ini}$ | 89.8 |
|  | $S_{end}$ | 88.8 |

The catalyst included 1 wt % of Pt and 3 wt % of Sn supported on CeO2, based on the weight of the CeO2. The CeO2 support was made by calcining cerium (III) nitrate hexahydrate (Sigma-Aldrich 202991). The catalyst was made by incipient wetness impregnation of 3 g of $CeO_2$ with 0.788 g of 8 wt % chloroplatinic acid in water (Sigma Aldrich, 262587) and 0.266 g of tin (IV) chloride pentahydrate (Acros Organics 22369), followed by drying and calcination at 800° C. for 12 h. The data in Table 9 shows that the catalyst was stable over 42 cycles.

Examples 25 and 26, Catalyst 3

The catalyst included 1 wt % of Pt and 2.7 wt % of Sn supported on Ceria-Zirconia, based on the weight of the Ceria-Zirconia. The Catalyst was made by incipient wetness impregnation of 16.5 g of Ceria-Zirconia (Sigma Aldrich 634174) with 0.44 g of chloroplatinic acid hexahydrate (BioXtra, P7082) and 1.33 g of tin (IV) chloride pentahydrate (Acros Organics 22369) dissolved in an appropriate amount of deionized water, followed by drying and calcination at 800° C. for 12 h. Results are shown in Table 10.

TABLE 9

|  |  | Ex. 24 |
|---|---|---|
| Catalyst |  | 2 |
| $M_{cat}$ (g) |  | 0.5 |
| $T_{rxn}$ (° C.) |  | 540 |
| $t_{rxn}$ (min) |  | 10 |
| $F_{rxn}$ (sccm) |  | 12.3 |
| $S_{vol}$ (vol %) |  | NA |
| $T_{red}$ (° C.) |  | NA |
| $t_{red}$ (min) |  | NA |
| $T_{regen}$ (° C.) |  | 540 |
| $t_{regen}$ (min) |  | 10 |
| Cycles |  | 42 |
| First | $Y_{ave}$ | 15 |
| cycle | $S_{ave}$ | 84.3 |
| Last | $Y_{ave}$ | 14.8 |
| cycle | $S_{ave}$ | 89.7 |

TABLE 10

|  |  | Ex. 25 | Ex. 26 |
|---|---|---|---|
| Catalyst |  | 3 | 3 |
| $M_{cat}$ (g) |  | 0.456 | 0.456 |
| $T_{rxn}$ (° C.) |  | 540 | 580 |
| $t_{rxn}$ (min) |  | 10 | 10 |
| $F_{rxn}$ (sccm) |  | 11 | 11 |
| $S_{vol}$ (vol %) |  | NA | NA |
| $T_{red}$ (° C.) |  | NA | NA |
| $t_{red}$ (min) |  | NA | NA |
| $T_{regen}$ (° C.) |  | 540 | 580 |
| $t_{regen}$ (min) |  | 10 | 10 |
| Cycles |  | 10 | 12 |
| First | $Y_{ini}$ | 22.2 | 28.6 |
| cycle | $Y_{end}$ | 10.6 | 9.9 |
|  | $S_{ini}$ | 85.5 | 75.9 |
|  | $S_{end}$ | 91.3 | 91 |
| Last | $Y_{ini}$ | 21.4 | 28.8 |
| cycle | $Y_{end}$ | 11.7 | 10.4 |
|  | $S_{ini}$ | 86.2 | 76.9 |
|  | $S_{end}$ | 91.3 | 91.1 |

Examples 27-29, Catalyst 4

The catalyst included 1 wt % of Pt and 2.7 wt % of Sn supported on $Y_2O_3$, based on the weight of the $Y_2O_3$. The catalyst was made by incipient wetness impregnation of 4 g of $Y_2O_3$(US nano 3553) with 0.106 g of chloroplatinic acid hexahydrate (BioXtra, P7082) and 0.322 g of tin (IV) chloride pentahydrate (Acros Organics 22369) dissolved in an appropriate amount of deionized water, followed by drying and calcination at 800° C. for 12 h. The data in Table 11 shows the performance of the catalyst was stable over 20 cycles.

Examples 30-34, Catalyst 5

The catalyst included 1 wt % of Pt, 2.7 wt % of Sn supported on a $CeO_2$ and $Al_2O_3$ support. The $CeO_2$ and $Al_2O_3$ support was made by incipient wetness impregnation of 8.25 g of alumina (Sigma Aldrich 199443) with 5.67 g of cerium (III) nitrate hexahydrate (Sigma Aldrich 202991) dissolved in an appropriate amount of deionized water, followed by drying and calcination at 800° C. for 12 h. The catalyst was made by incipient wetness impregnation of the $CeO_2$ and $Al_2O_3$ support with 0.22 g of chloroplatinic acid hexahydrate (BioXtra, P7082) and 0.67 g of tin (IV) chloride pentahydrate (Acros Organics 22369) dissolved in an appropriate amount of deionized water, followed by drying and calcination at 800° C. for 12 h. The data in Table 12 shows that both the co-addition of steam and catalyst pre-reduction helped to increase the yield and selectivity.

TABLE 11

|  |  | Ex. 27 | Ex. 28 | Ex. 29 |
|---|---|---|---|---|
| Catalyst |  | 4 | 4 | 4 |
| $M_{cat}$ (g) |  | 0.456 | 0.456 | 0.456 |
| $T_{rxn}$ (° C.) |  | 540 | 540 | 540 |
| $t_{rxn}$ (min) |  | 10 | 10 | 10 |
| $F_{rxn}$ (sccm) |  | 11 | 11 | 11 |
| $S_{vol}$ (vol %) |  | NA | NA | NA |
| $T_{red}$ (° C.) |  | NA | NA | 540 |
| $t_{red}$ (min) |  | NA | NA | 30 |
| $T_{regen}$ (° C.) |  | 540 | 540 | 540 |
| $t_{regen}$ (min) |  | 10 | 20 | 10 |
| Cycles |  | 20 | 1 | 1 |
| First | $Y_{ini}$ | 22.7 | 23.2 | 23.9 |
| cycle | $Y_{end}$ | 14.9 | 16 | 17.1 |
|  | $S_{ini}$ | 89.5 | 89.3 | 92.3 |
|  | $S_{end}$ | 94 | 94 | 94.8 |

TABLE 11-continued

|  |  | Ex. 27 | Ex. 28 | Ex. 29 |
|---|---|---|---|---|
| Last cycle | $Y_{ini}$ | 23.3 | NA | NA |
|  | $Y_{end}$ | 16.2 | NA | NA |
|  | $S_{ini}$ | 90.5 | NA | NA |
|  | $S_{end}$ | 94 | NA | NA |

TABLE 12

|  |  | Ex. 31 | Ex. 32 | Ex. 33 | Ex. 34 |
|---|---|---|---|---|---|
| Catalyst |  | 5 | 5 | 5 | 5 |
| $M_{cat}$ (g) |  | 0.228 | 0.228 | 0.228 | 0.228 |
| $T_{rxn}$ (° C.) |  | 620 | 620 | 620 | 620 |
| $t_{rxn}$ (min) |  | 10 | 10 | 10 | 10 |
| $F_{rxn}$ (sccm) |  | 17 | 17 | 17 | 17 |
| $S_{vol}$ (vol %) |  | NA | 11 | NA | 11 |
| $T_{red}$ (° C.) |  | 620 | NA | NA | 620 |
| $t_{red}$ (min) |  | 1 | NA | NA | 1 |
| $T_{regen}$ (° C.) |  | 620 | 620 | 620 | 620 |
| $t_{regen}$ (min) |  | 10 | 10 | 10 | 10 |
| Cycles |  | 1 | 1 | 1 | 1 |
| First cycle | $Y_{ini}$ | 27.8 | 25.8 | 9.2 | 33.5 |
|  | $Y_{end}$ | 24.6 | 20.9 | 3.1 | 29.2 |
|  | $S_{ini}$ | 91.5 | 90.9 | 89.3 | 92 |
|  | $S_{end}$ | 92.3 | 92.3 | 81.6 | 92.7 |

Examples 35-38, Catalyst 6

The catalyst was 0.2 wt % of Pt, 0.2 wt % of Sn, and 0.67 wt % of K on high surface area $ZrO_2$ obtained from Alfa Aesar. The data in Table 13 shows that the catalyst was stable over 24 cycles and that the addition of steam significantly enhanced the yield.

TABLE 13

|  |  | Ex. 35 | Ex. 36 | Ex. 37 | Ex. 38 |
|---|---|---|---|---|---|
| Catalyst |  | 6 | 6 | 6 | 6 |
| $M_{cat}$ (g) |  | 0.57 | 0.57 | 0.57 | 0.57 |
| $T_{rxn}$ (° C.) |  | 620 | 620 | 620 | 620 |
| $t_{rxn}$ (min) |  | 10 | 10 | 10 | 10 |
| $F_{rxn}$ (sccm) |  | 10 | 10 | 10 | 10 |
| $S_{vol}$ (vol %) |  | 11 | NA | NA | 1 |
| $T_{red}$ (° C.) |  | 620 | NA | 620 | 620 |
| $t_{red}$ (min) |  | 1 | NA | 1 | 1 |
| $T_{regen}$ (° C.) |  | 800 | 620 | 620 | 620 |
| $t_{regen}$ (min) |  | 30 | 30 | 30 | 30 |
| Cycles |  | 24 | 1 | 1 | 1 |
| First cycle | $Y_{ini}$ | 25.7 | 7 | 8.3 | 30.6 |
|  | $Y_{end}$ | 19.4 | 6.5 | 6.8 | 25.1 |
|  | $S_{ini}$ | 78.9 | 90.4 | 90.2 | 85.7 |
|  | $S_{end}$ | 78.4 | 90.6 | 90.2 | 84.2 |
| Last cycle | $Y_{ini}$ | 24.7 | NA | NA | NA |
|  | $Y_{end}$ | 19.5 | NA | NA | NA |
|  | $S_{ini}$ | 80.7 | NA | NA | NA |
|  | $S_{end}$ | 80.2 | NA | NA | NA |

Catalyst Compositions 7-20

Catalyst Compositions 7-20 were prepared according to the following procedure. For each catalyst composition PURALOX® MG 80/150 (3 grams) (Sasol), which was a mixed Mg/Al metal oxide that contained 80 wt % of MgO and 20 wt % of $Al_2O_3$ and had a surface area of 150 m²/g, was calcined under air at 550° C. for 3 hours to form a support. Solutions that contained a proper amount of tin (IV) chloride pentahydrate when used to make the catalyst composition (Acros Organics) and/or chloroplatinic acid when used to make the catalyst composition (Sigma Aldrich), and 1.8 ml of deionized water were prepared in small glass vials. The calcined PURALOX® MG 80/150 supports (2.3 grams) for each catalyst composition were impregnated with the corresponding solution. The impregnated materials were allowed to equilibrate in a closed container at room temperature (RT) for 24 hours, dried at 110° C. for 6 hours, and calcined at 800° C. for 12 hours.

Table 14 shows the nominal Pt and Sn content of each catalyst composition based on the weight of the support.

TABLE 14

| Catalyst | Pt (wt %) | Sn (wt %) |
|---|---|---|
| 7 | 0.4 | 1 |
| 8 | 0.3 | 1 |
| 9 | 0.2 | 1 |
| 10 | 0.1 | 1 |
| 11 | 0.05 | 1 |
| 12 | 0.025 | 1 |
| 13 | 0.0125 | 1 |
| 14 | 0 | 1 |
| 15 | 0.1 | 0.5 |
| 16 | 0.1 | 1 |
| 17 | 0.1 | 2 |
| 18 | 0.0125 | 0 |
| 19 | 0.0125 | 0.5 |
| 20 | 0.0125 | 2 |

Examples Using the Catalyst Compositions of Examples 7-20

Fixed bed experiments were conducted at approximately 100 kPa-absolute that used catalysts 7-14. A gas chromatograph (GC) was used to measure the composition of the reactor effluents. The concentrations of each component in the reactor effluents were then used to calculate the $C_3H_6$ yield and selectivity. The $C_3H_6$ yield and selectivity, as reported in these examples, were calculated on the carbon mole basis.

In each example, 0.3 g of the catalyst composition was mixed with an appropriate amount of quartz diluent and loaded into a quartz reactor. The amount of diluent was determined so that the catalyst bed (catalyst+diluent) overlapped with the isothermal zone of the quartz reactor and the catalyst bed was largely isothermal during operation. The dead volume of the reactor was filled with quartz chips/rods.

The $C_3H_6$ yield and the selectivity at the beginning of $t_x$ and at the end of $t_{rxn}$ is denoted as $Y_{ini}$, $Y_{end}$, $S_{ini}$, and $S_{end}$, respectively, and reported as percentages in Tables 5 and 6 below for catalysts 7-14.

The process steps for catalysts 7-14 were as follows: 1. The system was flushed with an inert gas. 2. Dry air at a flow rate of 83.9 sccm was passed through a by-pass of the reaction zone, while an inert was passed through the reaction zone. The reaction zone was heated to a regeneration temperature of 800° C. 3. Dry air at a flow rate of 83.9 sccm was then passed through the reaction zone for 10 min to regenerate the catalyst. 4. The system was flushed with an inert gas. 5. A $H_2$ containing gas with 10 vol % $H_2$ and 90 vol % Ar at a flow rate of 46.6 sccm was passed through the by-pass of the reaction zone for a certain period of time, while an inert gas was passed through the reaction zone. This is then followed by flowing the $H_2$ containing gas through the reaction zone at 800° C. for 3 seconds. 6. The system was flushed with an inert gas. During this process, the temperature of the reaction zone was changed from 800° C. to a reaction temperature of 670° C. 7. A hydrocarbon-containing (HCgas) feed that included 81 vol % of $C_3H_8$, 9 vol % of inert gas (Ar or Kr) and 10 vol % of steam at a flow rate of 35.2 sccm was passed through the by-pass of the reaction zone for a certain period of time, while an inert gas was passed through the reaction zone. The hydrocarbon-containing feed was then passed through the reaction zone at 670° C. for 10 min. GC sampling of the reaction effluent started as soon as the feed was switched from the by-pass of the reaction zone to the reaction zone.

The above process steps were repeated in cycles until stable performance was obtained. Tables 15 and 16 show that Catalyst 12 that contained only 0.025 wt % of Pt and 1 wt % of Sn had both a similar yield and a similar selectivity as compared to Catalyst 7 that contained 0.4 wt % of Pt and 1 wt % of Sn, which was surprising and unexpected. Catalyst 14 that did not include any Pt did not show an appreciable propylene yield.

TABLE 15

|  |  | Catalyst 7 | Catalyst 8 | Catalyst 9 | Catalyst 10 |
|---|---|---|---|---|---|
| Performance | $Y_{ini}$ | 61.7 | 61.7 | 60.7 | 63.7 |
|  | $Y_{end}$ | 55.2 | 55.7 | 54.2 | 56.7 |
|  | $S_{ini}$ | 97.3 | 97.2 | 97.0 | 97.1 |
|  | $S_{end}$ | 98.1 | 98.0 | 97.7 | 98.3 |

TABLE 16

|  |  | Catalyst 11 | Catalyst 12 | Catalyst 13 | Catalyst 14 |
|---|---|---|---|---|---|
| Performance | $Y_{ini}$ | 62.4 | 62.0 | 56.7 | 2.0 |
|  | $Y_{end}$ | 57.2 | 54.6 | 45.7 | 1.7 |
|  | $S_{ini}$ | 96.7 | 97.3 | 96.9 | 64.2 |
|  | $S_{end}$ | 97.7 | 98.0 | 97.6 | 49.5 |

Catalyst compositions 15-20 were also tested using the same process steps 1-7 described above with regard to catalysts 7-14. Table 17 shows that the level of Sn should not be too low or too high for optimal propylene yield for the catalyst compositions that included 0.1 wt % of Pt based on the weight of the support.

TABLE 17

|  |  | Catalyst 15 0.5 wt % Sn | Catalyst 10 1 wt % Sn | Catalyst 16 1 wt % Sn | Catalyst 17 2 wt % Sn |
|---|---|---|---|---|---|
| Performance | $Y_{ini}$ | 58.4 | 63.7 | 63.4 | 56.5 |
|  | $Y_{end}$ | 49.5 | 56.7 | 55.5 | 47.7 |
|  | $S_{ini}$ | 96.9 | 97.1 | 97.2 | 97.8 |
|  | $S_{end}$ | 97.6 | 98.3 | 98.1 | 98.2 |

Table 18 shows that the level of Sn should not be too high or too low for optimal propylene yield for the catalyst compositions that included 0.0125 wt % of Pt based on the weight of the support.

TABLE 18

|  |  | Catalyst 18 0 wt % Sn | Catalyst 19 0.5 wt % Sn | Catalyst 13 1 wt % Sn | Catalyst 20 2 wt % Sn |
|---|---|---|---|---|---|
| Performance | $Y_{ini}$ | 2.6 | 44 | 56.7 | 55.4 |
|  | $Y_{end}$ | 1.7 | 24.4 | 45.7 | 44.1 |
|  | $S_{ini}$ | 63.9 | 96.7 | 96.9 | 96.8 |
|  | $S_{end}$ | 61.1 | 95.6 | 97.6 | 97.6 |

Figure 4:
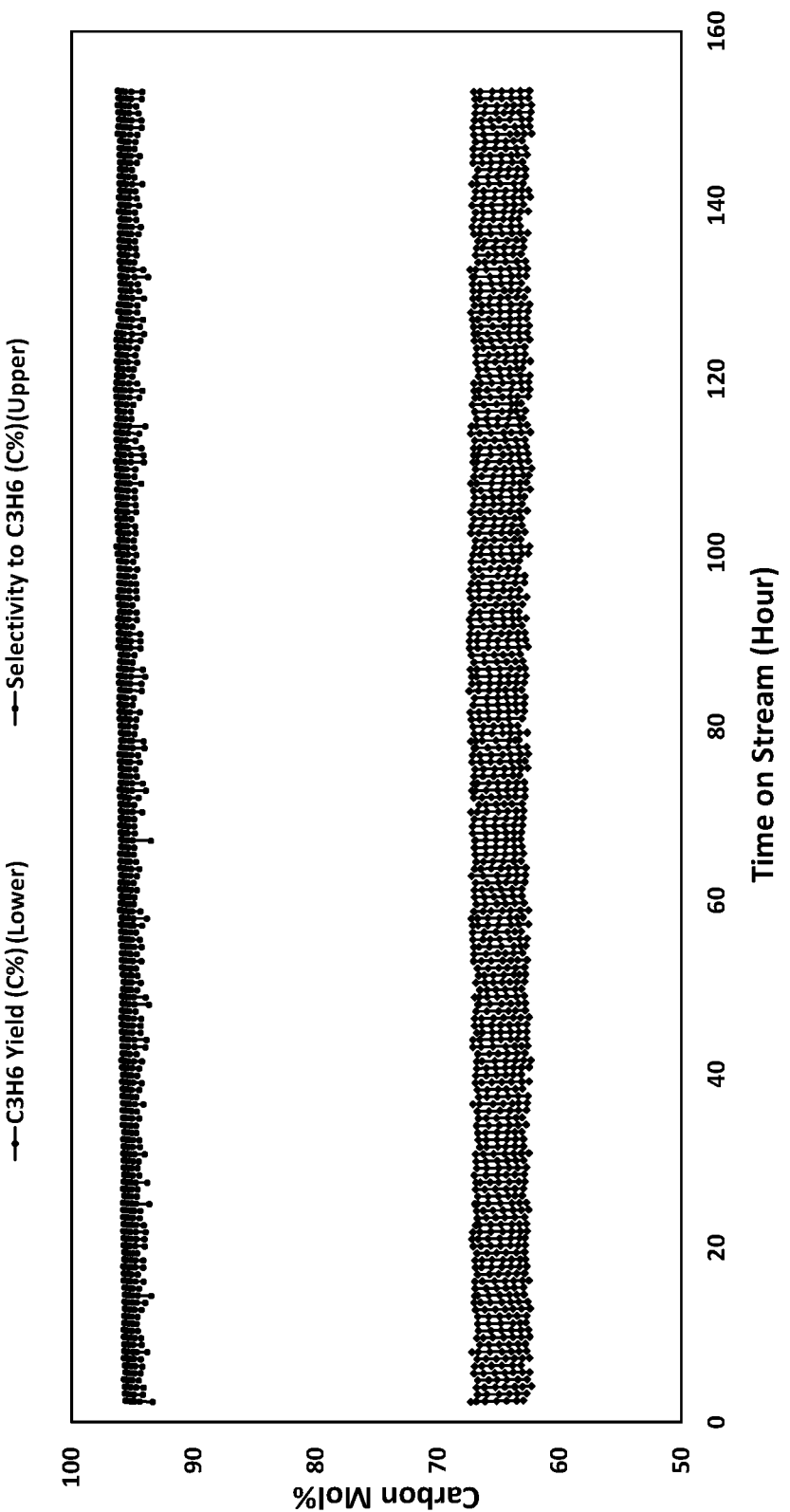
FIG. 4 shows a catalyst composition (catalyst 12) maintained its performance for 204 cycles.

Catalyst composition 12 that contained only 0.025 wt % of Pt and 1 wt % of Sn was also subjected to a longevity test using the same process steps 1-7 described above with regard to catalysts 7 to 14, except a flow rate of 17.6 sccm was used instead of 35.2 sccm in step 7. FIG. 4 shows that catalyst composition 12 maintained performance for 204 cycles (x-axis is time, y-axis is $C_3H_6$ yield and selectivity to $C_3H_6$, both in carbon mole %).

Listing of Embodiments

This disclosure may further include the following non-limiting embodiments.

A1. A process for upgrading a hydrocarbon, comprising: (I) introducing a hydrocarbon-containing feed comprising one or more of $C_2$-$C_{16}$ linear or branched alkanes, one or more of $C_4$-$C_{16}$ cyclic alkanes, one or more of $C_8$-$C_{16}$ alkyl aromatics, or a mixture thereof into a reaction zone; (II) contacting the hydrocarbon-containing feed with a catalyst disposed within the reaction zone to effect at least one of dehydrogenation, dehydroaromatization, and dehydrocyclization of at least a portion of the hydrocarbon-containing feed to produce a coked catalyst and a first effluent comprising one or more upgraded hydrocarbons and molecular hydrogen, wherein the hydrocarbon-containing feed and the catalyst are contacted at a temperature in a range from 300° C. to 900° C., for a time period of 1 minute to 90 minutes, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed, wherein the catalyst comprises a Group 8-10 element or a compound thereof disposed on a support; (III) halting introduction of the hydrocarbon-containing feed into the reaction zone; (IV) introducing an oxidant into the reaction zone; (V) contacting the oxidant with the coked catalyst to effect combustion of at least a portion of the coke to produce a regenerated catalyst lean in coke and a second effluent comprising a combustion gas, wherein the oxidant and the coked catalyst are contacted for a time period of 1 minute to 90 minutes; (VI) halting introduction of the oxidant into the reaction zone; (VII) introducing a reducing gas into the reaction zone; (VIII) contacting the reducing gas with the regenerated catalyst to produce a regenerated and reduced catalyst and a third effluent, wherein the reducing gas and the regenerated catalyst are contacted for a time period of 0.1 seconds to 90 minutes; (IX) halting introduction of the reducing gas into the reaction zone; (X) introducing an additional quantity of the hydrocarbon-containing feed into the reaction zone; and (XI) contacting the additional quantity of the hydrocarbon-containing feed with the regenerated and reduced catalyst to produce a re-coked catalyst and additional first effluent, wherein the additional quantity of the hydrocarbon-containing feed and the regenerated and reduced catalyst are contacted at a temperature in a range from 300° C. to 900° C., for a time period of 1 minute to 90 minutes, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed.

A2. The process of A1, wherein the support comprises: at least one of: w wt % of one or more Group 2 elements, x wt % of one or more Group 4 elements, y wt % of one or more Group 12 elements, and z wt % of one or more elements having an atomic number of 21, 39, or 57-71, based on the weight of the support, wherein w, x, y, and z are independently in a range from 0 to 100, and wherein w+x+y+z is ≤100, wherein: any Group 2 element present is associated with a wt % m based on the weight of the support, any Group 4 element present is associated with a wt % n based on the weight of the support, any group 12 element present is associated with a wt % p based on the weight of the support, and any element having an atomic number of 21, 39, or 57-71 present is associated with a wt % q based on the weight of the support, m, n, p, and q are independently a number that is in a range from 1 to 100, a sum of w/m+x/n+y/p+z/q is ≥1, based on the weight of the support, and the catalyst comprises 0.001 wt % to 6 wt % of the Group 8-10 element or the compound thereof based on the weight of the support.

A3. The process of A1 or A2, wherein an inverse temperature profile or an isothermal temperature profile is maintained within the reaction zone during step (II).

A4. The process of any of A1 to A3, wherein the catalyst is disposed in a fixed bed within the reaction zone.

A5. The process of any of A1 to A3, wherein the catalyst is in the form of a plurality of discrete particles within the reaction zone.

A6. The process of A5, wherein a flow of the hydrocarbon-containing feed through the reaction zone, a flow of the oxidant through the reaction zone, and a flow of the reducing gas through the reaction zone are such that a superficial gas velocity is sufficient to fluidize the plurality of discrete particles but is below a velocity required for dilute-phase pneumatic conveying of the plurality of discrete particles in order to maintain a catalyst bed with a void fraction below 95%.

A7. The process of any of A1 to A6, wherein the hydrocarbon-containing feed and the oxidant flow through the reaction zone in the same direction.

A8. The process of any of A1 to A7, wherein the hydrocarbon-containing feed and the oxidant flow through the reaction zone in opposite directions.

A9. The process of any of A1 to A8, wherein: the hydrocarbon-containing feed comprises propane, the hydrocarbon-containing feed is at a temperature in a range from 300° C. to 700° C. when introduced into the reaction zone, the hydrocarbon-containing feed has a hydrocarbon partial pressure of 20 kPa-absolute to 1,000 kPa-absolute, and the first effluent is at a temperature in a range from 500° C. to 800° C. upon exiting the reaction zone.

A10. The process of any of A1 to A9, wherein, upon exiting the reaction zone, the first effluent is at a temperature of ≥580° C., more preferably ≥630° C., or more preferably ≥670° C.

A11. The process of any of A1 to A10, wherein: the hydrocarbon-containing feed comprises propane, the upgraded hydrocarbon comprises propylene, and step (III) is initiated when the temperature of the first effluent upon exiting the reaction zone falls below 710° C., 680° C., 650° C., 620° C., 610° C., 600° C., 590° C., 580° C., 570° C., 560° C., or 550° C.

A12. The process of any of A1 to A11, wherein: the hydrocarbon-containing feed comprises propane, the upgraded hydrocarbon comprises propylene, contacting the hydrocarbon-containing feed with the catalyst in step (II) has a propylene selectivity of ≥75%, and step (III) is initiated when a propylene yield falls below 65%, 50%, 55%, 50%, 47%, 45%, 43%, 40%, 37%, or 35%.

A13. The process of any of A1 to A12, wherein: steps (I) to (XI) are repeated for at least 15 cycles, the catalyst produces a first yield when initially contacted with the hydrocarbon-containing feed, and upon completion of the fifteenth cycle, the catalyst produces a fifteenth yield that is at least 98% of the first yield.

A14. The process of any of A1 to A13, wherein: the hydrocarbon-containing feed comprises propane, the upgraded hydrocarbon comprises propylene, and contacting the hydrocarbon-containing feed with the catalyst in step (II) has a propylene yield of at least 52%, or at least 62%, or at least 72% at a propylene selectivity of ≥75%, ≥80%, ≥85%, or ≥90%, ≥95%.

A15. The process of any of A1 to A14, wherein the hydrocarbon-containing feed introduced into the reaction zone comprises steam in an amount from 0.1 vol % to 50 vol %, preferably from 0.5 vol % to 20 vol %, more preferably from 1 vol % to 15 vol %, or more preferably from 5 vol % to 10 vol %, based on a total volume of any $C_2$-$C_{16}$ alkanes and any $C_8$-$C_{16}$ alkyl aromatics in the hydrocarbon-containing feed.

A16. The process of any of A1 to A15, further comprising, after step (III) and before step (IV), the following step: (IIIa1) introducing a stripping gas into the reaction zone to remove at least a portion of any residual hydrocarbon-containing feed, first effluent, or both from the reaction zone; (IIIa2) removing at least a portion of any residual hydrocarbon containing feed, effluent, or both from the reaction zone by subjecting the reaction zone to a pressure of less than atmospheric pressure; or a combination of steps (IIIa1) and (IIIa2).

A17. The process of any of A1 to A16, further comprising, after step (VI) and before step (VII), the following step: (VIa1) introducing a stripping gas into the reaction zone to remove at least a portion of any residual oxidant, second effluent, or both from the reaction zone; (VIa2) removing at least a portion of any residual oxidant, second effluent, or both from the reaction zone by subjecting the reaction zone to a pressure of less than atmospheric pressure; or a combination of steps (VIa1) and (VIa2).

A18. The process of any of A1 to A17, further comprising, after step (IX) and before step (X), the following step: (IXa1) introducing a stripping gas into the reaction zone to remove at least a portion of any residual reducing gas, third effluent, or both from the reaction zone; (IXa2) removing at least a portion of any residual reducing gas, third effluent, or both from the reaction zone by subjecting the reaction zone to a pressure of less than atmospheric pressure; or a combination of steps (IXa1) and (IXa2).

A19. The process of any of A1 to A18, wherein step (IV) further comprises: introducing a fuel with the oxidant into the reaction zone; and combusting at least a portion of the fuel within the reaction zone to produce heat that heats the reaction zone to a temperature of ≥580° C., ≥620° C., ≥650° C., ≥680° C., ≥710° C., ≥740° C., ≥770° C., ≥800° C., ≥850° C., ≥900° C., or ≥1,000° C.

A20. The process of any of A1 to A19, wherein the oxidant is at a temperature in a range from 580° C. to 1,100° C., preferably from 600° C. to 1,000° C., more preferably from 700° C. to 900° C., or more preferably from 750° C. to 850° C. and at a pressure in a range from 20 kPa-absolute to 1,000 kPa-absolute when contacted with the coked catalyst.

A21. The process of any of A1 to A20, wherein the oxidant comprises molecular oxygen, ozone, carbon dioxide, steam, or a mixture thereof.

A22. The process of any of A1 to A21, wherein the reducing gas is at a temperature in a range from 450° C. to 900° C., preferably from 600° C. to 900° C., more preferably from 620° C. to 900° C., more preferably from 650° C. to 850° C., or more preferably from 670° C. to 800° C. when contacted with the regenerated catalyst.

A23. The process of any of A1 to A22, wherein the reducing gas comprises molecular hydrogen, carbon monoxide, methane, ethane, ethylene, propane, propylene, steam, molecular nitrogen, argon, carbon dioxide, or a mixture thereof.

A24. The process of any of A1 to A23, wherein a heat-storing material is disposed within the reaction zone, and wherein the heat-storing material releases at least a portion of stored heat during step (II) and stores heat produced during any of the additional steps.

A25. The process of A24, wherein the heat-storing material comprises quartz, silicon carbide, aluminum nitride, silicon nitride, boron carbide, alumina, or a mixture thereof.

A26. The process of any of A1 to A25, wherein a heat-generating material configured to generate heat during at least one step is disposed within the reaction zone.

A27. The process of A26, wherein the heat-generating material comprises a metal in oxide form supported on a carrier, wherein the metal is selected from the group consisting of: an alkali metal, an alkaline earth metal, copper, chromium, molybdenum, vanadium, cerium, yttrium, scandium, tungsten, manganese, iron, cobalt, nickel, silver, bismuth, and a combination thereof.

A28. The process of A27, wherein the carrier in the heat-generating material is selected from the group consisting of: aluminum oxides, aluminum hydroxides, aluminum trihydroxide, boehmite, pseudo-boehmite, gibbsite, bayerite, transition aluminas, alpha-alumina, gamma-alumina, silica/alumina, silica, silicates, aluminates, calcium aluminate, barium hexaaluminate, calcined hydrotalcites, zeolites, zinc oxide, chromium oxides, magnesium oxides, zirconia oxides, and combinations thereof.

A29. The process of any of A1 to A28, wherein a selective hydrogen removal material configured to selectively combust or absorb molecular hydrogen during step (II) is disposed within the reaction zone.

A30. The process of A29, wherein the selective hydrogen removal material comprises a metal in oxide form supported on a carrier, wherein the metal is selected from the group consisting of: an alkali metal, an alkaline earth metal, copper, chromium, molybdenum, vanadium, cerium, yttrium, scandium, tungsten, manganese, iron, cobalt, nickel, silver, bismuth, and a combination thereof.

A31. The process of A30, wherein the carrier in the selective hydrogen removal material is selected from the group consisting of: aluminum oxides, aluminum hydroxides, aluminum trihydroxide, boehmite, pseudo-boehmite, gibbsite, bayerite, transition aluminas, alpha-alumina, gamma-alumina, silica/alumina, silica, silicates, aluminates, calcium aluminate, barium hexaaluminate, calcined hydrotalcites, zeolites, zinc oxide, chromium oxides, magnesium oxides, zirconia oxides, and a combination thereof.

A32. The process any of A29 to A31, wherein the selective hydrogen removal material further comprises a promoter.

A33. The process of A32, wherein the promoter in the selective hydrogen removal material comprises one or more alkali metal oxides or salts thereof, one or more alkaline earth metal oxides or salts thereof, or a mixture or combination thereof.

A34. The process of any of A29 to A33, wherein the selective hydrogen removal material comprises a metal or metal alloy selected from the group consisting of: Zr, Sc, Ti, Zr, V, Nb, Hf, Co, Mg, La, Pd, Ni, Fe, Cu, Ag, Cr, and Th.

A35. The process of any of A1 to A34, wherein the reaction zone comprises a hydrogen permeation membrane disposed therein and configured to selectively remove molecular hydrogen from the reaction zone.

A36. The process of any of A1 to A34, further comprising introducing an oxidant into the reaction zone during introduction of the hydrocarbon-containing feed, wherein the oxidant reacts with molecular hydrogen produced within the reaction zone to produce $H_2O$.

A37. The process of any of A1 to A36, wherein the catalyst further comprises a promoter.

A38. The process of A37, wherein the promoter in the catalyst comprises one or more of the following elements: Sn, Ga, Zn, Ge, In, Re, Ag, Au, Cu, a combination thereof, or a mixture thereof.

A39. The process of A37 or A38, wherein the promoter in the catalyst is disposed on the support.

A40. The process of any of A37 to A39, wherein the promoter in the catalyst is associated with the Group 8-10 element.

A41. The process of any of A37 to A40, wherein the promoter in the catalyst and the Group 8-10 element form Group 8-10 element-promoter clusters that are dispersed on the support.

A42. The process of any of A37 to A41, wherein the catalyst comprises up to 10 wt % of the promoter based on the total weight of the support.

A43. The process of any of A1 to A42, wherein the catalyst further comprises an alkali metal element disposed on the support.

A44. The process of A43, wherein the alkali metal element comprises one or more of the following: Li, Na, K, Rb, Cs, a combination thereof, or a mixture thereof.

A45. The process of A43 or A44, and wherein the catalyst comprises up to 5 wt % of the alkali metal element based on the total weight of the support.

A46. The process of any of A2 to A45, wherein m, n, p, and q are each equal to 1, 2, 15, or 30, or wherein m=1, n=15, p=15, and q=1.

A47. The process of any of A2 to A46, wherein a molar ratio of a combined amount of any Group 2 element, any Group 4 element, any Group 12 element, and any element having an atomic number of 21, 39, or 57-71 to the Group 8-10 element in the catalyst is at least 0.18, at least 0.19, at least 0.24, or at least 0.29.

A48. The process of any of A2 to A47, wherein the support in the catalyst further comprises at least one compound comprising at least one metal element or metalloid element selected from Groups 5, 6, 7, 11, 13, 14, 15, and 16.

A49. The process of any of A2 to A48, wherein at least a portion of any Group 2 element, at least a portion of any Group 4 element, at least a portion of any Group 12 element, and at least a portion of any element having an atomic number of 21, 39, or 57-71 present in the support is an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide.

A50. The process of any of A2 to A49, wherein the support in the catalyst comprises one or more of the following: $Mg_uZn_{1-u}O$, where u is a positive number; $Zn_vAl2O3_{+v}$, where v is a positive number; $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number; BeO; MgO; CaO; BaO; SrO; $BeCO_3$; $MgCO_3$; $CaCO_3$; $SrCO_3$; $BaCO_3$; $ZrO_2$; ZrC; ZrN; $ZrSiO_4$; $CaZrO_3$; $Ca_7ZrAl_6O_{18}$; $TiO_2$; TiC; TiN; $TiSiO_4$; $CaTiO_3$; $Ca_7Al_6O_{18}$; $HfO_2$; HfC; HfN; $HfSiO_4$;

HfZrO$_3$; Ca$_7$HfAl$_6$O$_{18}$; ZnO; Zn$_3$(PO$_4$)$_2$; Zn(ClO$_3$)$_2$; ZnSO$_4$; B$_2$O$_6$Zn$_3$; Zn$_3$N$_2$; ZnCO$_3$; CeO$_2$; Y$_2$O$_3$; La$_2$O$_3$; Sc$_2$O$_3$; Pr$_6$O$_{11}$; CePO$_4$; CeZrO$_4$; CeAlO$_3$; BaCeO$_3$; CePO$_4$; Yttria-stabilized ZrO$_2$; combinations thereof, and mixtures thereof A51. The process of any of A2 to A50, wherein the support in the catalyst further comprises one or more of the following: B$_2$O$_3$, AlBO$_3$, Al$_2$O$_3$, SiO$_2$, SiC, Si$_3$N$_4$, an aluminosilicate, VO, V$_2$O$_3$, VO$_2$, V$_2$O$_5$, Ga$_2$O$_3$, In$_2$O$_3$, Mn$_2$O$_3$, Mn$_3$O$_4$, MnO; a zeolite; combinations thereof; and mixture thereof.

A52. The process of any of A2 to A51, wherein the Group 8-10 element comprises Pt.

A53. The process of any of A1 to A52, wherein the hydrocarbon-containing feed comprises ethane, propane, isobutane, butane, ethylbenzene, propylbenzene, methylethylbenzene, or a mixture thereof.

A54. The process of any of A1 to A53, wherein, during normal operation, the oxidant contacts the coked catalyst in step (V) at a normal temperature, a normal pressure, and for a normal period of time, the process further comprising every 12 hours to 90 days modifying step (V) by increasing the normal temperature, increasing the normal pressure, increasing the normal period of time, or a combination thereof to effect a re-activation of the coked catalyst.

A55. The process of any of A1 to A54, wherein the support comprises ≥3 wt %, ≥6 wt %, ≥11 wt %, ≥15 wt %, or ≥20 wt % of a Group 2 element.

A56. The process of A 55, wherein the Group 2 element comprises Mg.

A57. The process of any of A1 to A56, wherein the support comprises calcined hydrotalcite.

A58. The process of any of A1 to A57, wherein the reaction zone is a first reaction zone and the catalyst is a first catalyst, the process further comprising: carrying out steps (I)-(XI) within a second reaction zone comprising a second catalyst; and carrying out steps (I)-(XI) within a third reaction zone comprising a third catalyst, wherein the first reaction zone, the second reaction zone, and the third reaction zone are operated in parallel, and wherein a timing of the steps (I)-(XI) between the first, second, and third reaction zones is such that there is a continuous production of the one or more upgraded hydrocarbons and molecular hydrogen across the first, second, and third reaction zones.

A59. The process of A58, wherein the first catalyst, the second catalyst, and the third catalyst have the same composition.

B1. A cyclic process for upgrading a hydrocarbon in a reactor system, comprising: (I) a reaction interval comprising introducing and halting introduction of a hydrocarbon-containing feed into a reaction zone, wherein the hydrocarbon-containing feed comprises one or more of C$_2$-C$_{16}$ linear or branched alkanes, one or more of C$_4$-C$_{16}$ cyclic alkanes, one or more of C$_8$-C$_{16}$ alkyl aromatics, or a mixture thereof; (II) a regeneration interval following the reaction interval, the regeneration interval comprising introducing and halting introduction of an oxidant into the reaction zone; and (III) a reduction interval following the regeneration interval, the reduction interval comprising introducing and halting introduction of a reducing gas into the reaction zone; wherein: the reaction interval is restarted after the reduction interval; during introduction of the hydrocarbon-containing feed into the reaction zone, the hydrocarbon-containing feed contacts a catalyst disposed within the reaction zone to effect at least one of dehydrogenation, dehydroaromatization, and dehydrocyclization of at least a portion of the hydrocarbon-containing feed to produce a coked catalyst and a first effluent comprising one or more upgraded hydrocarbons and molecular hydrogen, wherein the hydrocarbon-containing feed and the catalyst are contacted at a temperature in a range from 300° C. to 900° C., for a time period of 1 minute to 90 minutes, under a hydrocarbon partial pressure of at least 20 kPa-absolute, wherein the hydrocarbon partial pressure is the total partial pressure of any C$_2$-C$_{16}$ alkanes and any C$_8$-C$_{16}$ alkyl aromatics in the hydrocarbon-containing feed; during introduction of the oxidant into the reaction zone, the oxidant contacts the coked catalyst to effect combustion of at least a portion of the coke to produce a regenerated catalyst lean in coke and a second effluent comprising a combustion gas, wherein the oxidant and the coked catalyst are contacted for a time period of 1 minute to 90 minutes; during introduction of the reducing gas into the reaction zone, the reducing gas contacts the regenerated catalyst to produce a regenerated and reduced catalyst; the catalyst comprises a Group 8-10 element or a compound thereof disposed on a support.

B2. The process of B1, wherein the support comprises: at least one of: w wt % of one or more Group 2 elements, x wt % of one or more Group 4 elements, y wt % of one or more Group 12 elements, and z wt % of one or more elements having an atomic number of 21, 39, or 57-71, based on the weight of the support, wherein w, x, y, and z are independently in a range from 0 to 100, and wherein w+x+y+z is ≤100, wherein: any Group 2 element present is associated with a wt % m based on the weight of the support, any Group 4 element present is associated with a wt % n based on the weight of the support, any group 12 element present is associated with a wt % p based on the weight of the support, and any element having an atomic number of 21, 39, or 57-71 present is associated with a wt % q based on the weight of the support, m, n, p, and q are independently a number that is in a range from 1 to 100, a sum of w/m+x/n+y/p+z/q is ≥1, based on the weight of the support, and the catalyst comprises 0.001 wt % to 6 wt % of the Group 8-10 element or the compound thereof based on the weight of the support.

B3. The process of B1 or B2, wherein an inverse temperature profile or an isothermal temperature profile is maintained within the reaction zone during the reaction interval.

B4. The process of any of B1 to B3, wherein the catalyst is disposed in a fixed bed within the reaction zone.

B5. The process of any of B1 to B3, wherein the catalyst is in the form of a plurality of discrete particles within the reaction zone.

B6. The process of B5, wherein a flow of the hydrocarbon-containing feed through the reaction zone, a flow of the oxidant through the reaction zone, and a flow of the reducing gas through the reaction zone are such that a superficial gas velocity is sufficient to fluidize the plurality of discrete particles but is below a velocity required for dilute-phase pneumatic conveying of the plurality of discrete particles in order to maintain a catalyst bed with void fraction below 95%.

B7. The process of any of B1 to B6, wherein the hydrocarbon-containing feed and the oxidant flow through the reaction zone in the same direction.

B8. The process of any of B1 to B6, wherein the hydrocarbon-containing feed and the oxidant flow through the reaction zone in opposite directions.

B9. The process of any of B1 to B8, wherein: the hydrocarbon-containing feed comprises propane, the hydrocarbon-containing feed is at a temperature in a range from 300° C. to 700° C. when introduced into the reaction zone, the hydrocarbon-containing feed has a hydrocarbon partial pressure of 20 kPa-absolute to 1,000 kPa-absolute, and the first effluent is at a temperature in a range from 500° C. to 800° C. upon exiting the reaction zone.

B10. The process of any of B1 to B9, wherein, upon exiting the reaction zone, the first effluent is at a temperature of ≥580° C., more preferably ≥630° C., or more preferably ≥670° C.

B11. The process of any of B1 to B10, wherein: the hydrocarbon-containing feed comprises propane, the upgraded hydrocarbon comprises propylene, and introduction of the hydrocarbon-containing feed into the reaction zone during the reaction interval is halted when the temperature of the first effluent upon exiting the reaction zone falls below 710° C., 680° C., 650° C., 620° C., 610° C., 600° C., 590° C., 580° C., 570° C., 560° C., or 550° C.

B12. The process of any of B1 to B11, wherein: the hydrocarbon-containing feed comprises propane, the upgraded hydrocarbon comprises propylene, contacting the hydrocarbon-containing feed with the catalyst in step (I) has a propylene selectivity of ≥75%, and introduction of the hydrocarbon-containing feed into the reaction zone during the reaction interval is halted when a propylene yield falls below 65%, 50%, 55%, 50%, 47%, 45%, 43%, 40%, 37%, or 35%.

B13. The process of any of B1 to B12, wherein: the reaction interval, the regeneration interval, and the reduction interval are repeated for at least 15 cycles, the catalyst produces a first yield when initially contacted with the hydrocarbon-containing feed, and upon completion of the fifteenth cycle, the catalyst produces a fifteenth yield that is at least 98% of the first yield.

B14. The process of any of B1 to B13, wherein: the hydrocarbon-containing feed comprises propane, the upgraded hydrocarbon comprises propylene, and contacting the hydrocarbon-containing feed with the catalyst during the reaction interval has a propylene yield of at least 52%, or at least 62%, or at least 72% at a propylene selectivity of ≥75%, ≥80%, ≥85%, or ≥90%, ≥95%.

B15. The process of any of B1 to B14, wherein the hydrocarbon-containing feed introduced into the reaction zone comprises steam in an amount from 0.1 vol % to 50 vol %, preferably from 0.5 vol % to 20 vol %, more preferably from 1 vol % to 15 vol %, or more preferably from 5 vol % to 10 vol %, based on a total volume of any $C_2$-$C_{16}$ alkanes and any $C_8$-$C_{16}$ alkyl aromatics in the hydrocarbon-containing feed.

B16. The process of any of B1 to B15, further comprising, after the reaction interval and before the regeneration interval, the following step: (Ia1) a stripping interval comprising introducing and halting introduction of a stripping gas into the reaction zone to remove at least a portion of any residual hydrocarbon-containing feed, first effluent, or both from the reaction zone; (Ia2) a vacuum interval comprising removing at least a portion of any residual hydrocarbon containing feed, effluent, or both from the reaction zone by subjecting the reaction zone to a pressure of less than atmospheric pressure; or a combination of steps (Ia1) and (Ia2).

B17. The process of any of B1 to B16, further comprising, after the regeneration interval and before the reduction interval, the following step: (IIa1) a stripping interval comprising introducing and halting introduction of a stripping gas into the reaction zone to remove at least a portion of any residual oxidant, second effluent, or both from the reaction zone; (IIa2) a vacuum interval comprising removing at least a portion of any residual oxidant, second effluent, or both from the reaction zone by subjecting the reaction zone to a pressure of less than atmospheric pressure; or a combination of steps (IIa1) and (IIa2).

B18. The process of any of B1 to B17, further comprising, after the reduction interval and before repeating the reaction interval, the following step: (IIIa1) a stripping interval comprising introducing and halting introduction of a stripping gas into the reaction zone to remove at least a portion of any residual reducing gas, third effluent, or both from the reaction zone; (IIIa2) a vacuum interval comprising removing at least a portion of any residual reducing gas, third effluent, or both from the reaction zone by subjecting the reaction zone to a pressure of less than atmospheric pressure; or a combination of steps (IIIa1) and (IIIa2).

B19. The process of any of B1 to B18, wherein the regeneration interval further comprises: introducing a fuel with the oxidant into the reaction zone; and combusting at least a portion of the fuel within the reaction zone to produce heat that heats the reaction zone to a temperature of ≥580° C., ≥620° C., ≥650° C., ≥680° C., ≥710° C., ≥740° C., ≥770° C., ≥800° C., ≥850° C., ≥900° C., or ≥1,000° C.

B20. The process of any of B1 to B19, wherein the oxidant is at a temperature in a range from 580° C. to 1,100° C., preferably from 600° C. to 1,000° C., more preferably from 700° C. to 900° C., or more preferably from 750° C. to 850° C. and at a pressure in a range from 20 kPa-absolute to 1,000 kPa-absolute when contacted with the coked catalyst.

B21. The process of any of B1 to B20, wherein the oxidant comprises molecular oxygen, ozone, carbon dioxide, steam, or a mixture thereof.

B22. The process of any of B1 to B21, wherein the reducing gas is at a temperature in a range from 450° C. to 900° C., preferably from 600° C. to 900° C., more preferably from 620° C. to 900° C., more preferably from 650° C. to 850° C., or more preferably from 670° C. to 800° C. when contacted with the regenerated catalyst.

B23. The process of any of B1 to B22, wherein the reducing gas comprises molecular hydrogen, carbon monoxide, methane, ethane, ethylene, propane, propylene, steam, molecular nitrogen, argon, carbon dioxide, or a mixture thereof.

B24. The process of any of B1 to B23, wherein a heat-storing material is disposed within the reaction zone, and wherein the heat-storing material releases at least a portion of stored heat during the reaction interval and stores at least a portion of any heat produced during the regeneration interval and at least a portion of any heat produced during the reduction interval.

B25. The process of B24, wherein the heat-storing material comprises quartz, silicon carbide, aluminum nitride, silicon nitride, boron carbide, alumina, or a mixture thereof.

B26. The process of any of B1 to B25, wherein a heat-generating material configured to generate heat during at least one of the reaction interval, the regeneration interval, and the reduction interval is disposed within the reaction zone.

B27. The process of B26, wherein the heat-generating material comprises a metal in oxide form supported on a carrier, wherein the metal is selected from the group consisting of: an alkali metal, an alkaline earth metal, copper, chromium, molybdenum, vanadium, cerium, yttrium, scandium, tungsten, manganese, iron, cobalt, nickel, silver, bismuth, and a combination thereof.

B28. The process of B27, wherein the carrier in the heat-generating material is selected from the group consisting of: aluminum oxides, aluminum hydroxides, aluminum trihydroxide, boehmite, pseudo-boehmite, gibbsite, bayerite, transition aluminas, alpha-alumina, gamma-alumina, silica/alumina, silica, silicates, aluminates, calcium aluminate, barium hexaaluminate, calcined hydrotalcites, zeolites, zinc oxide, chromium oxides, magnesium oxides, zirconia oxides, and combinations thereof.

B29. The process of any of B1 to B28, wherein a selective hydrogen removal material configured to selectively combust or absorb molecular hydrogen during the reaction interval is disposed within the reaction zone.

B30. The process of B29, wherein the selective hydrogen removal material comprises a metal in oxide form supported on a carrier, wherein the metal is selected from the group consisting of: an alkali metal, an alkaline earth metal, copper, chromium, molybdenum, vanadium, cerium, yttrium, scandium, tungsten, manganese, iron, cobalt, nickel, silver, bismuth, and a combination thereof.

B31. The process of B30, wherein the carrier in the selective hydrogen removal material is selected from the group consisting of: aluminum oxides, aluminum hydroxides, aluminum trihydroxide, boehmite, pseudo-boehmite, gibbsite, bayerite, transition aluminas, alpha-alumina, gamma-alumina, silica/alumina, silica, silicates, aluminates, calcium aluminate, barium hexaaluminate, calcined hydrotalcites, zeolites, zinc oxide, chromium oxides, magnesium oxides, zirconia oxides, and a combination thereof.

B32. The process any of B29 to B31, wherein the selective hydrogen removal material further comprises a promoter.

B33. The process of B32, wherein the promoter in the selective hydrogen removal material comprises one or more alkali metal oxides or salts thereof, one or more alkaline earth metal oxides or salts thereof, or a mixture or combination thereof.

B34. The process of any of B29 TO B33, wherein the selective hydrogen removal material comprises a metal or metal alloy selected from the group consisting of: Zr, Sc, Ti, Zr, V, Nb, Hf, Co, Mg, La, Pd, Ni, Fe, Cu, Ag, Cr, and Th.

B35. The process of any of B1 to B34, wherein the reaction zone comprises a hydrogen permeation membrane disposed therein and configured to selectively remove molecular hydrogen from the reaction zone.

B36. The process of any of B1 to B35, further comprising introducing an oxidant into the reaction zone during introduction of the hydrocarbon-containing feed, wherein the oxidant reacts with molecular hydrogen produced within the reaction zone to produce $H_2O$.

B37. The process of any of B2 to B36, wherein the catalyst further comprises a promoter.

B38. The process of B37, wherein the promoter in the catalyst comprises one or more of the following elements: Sn, Ga, Zn, Ge, In, Re, Ag, Au, Cu, a combination thereof, or a mixture thereof.

B39. The process of B37 or B38, wherein the promoter in the catalyst is disposed on the support.

B40. The process of any of B37 to B39, wherein the promoter in the catalyst is associated with the Group 8-10 element.

B41. The process of any of B37 to B40, wherein the promoter in the catalyst and the Group 8-10 element form Group 8-10 element-promoter clusters that are dispersed on the support.

B42. The process of any of B37 to B41, wherein the catalyst comprises up to 10 wt % of the promoter based on the total weight of the support.

B43. The process of any of B2 to B42, wherein the catalyst further comprises an alkali metal element disposed on the support.

B44. The process of B43, wherein the alkali metal element comprises one or more of the following: Li, Na, K, Rb, Cs, a combination thereof, or a mixture thereof.

B45. The process of B43 or B44, and wherein the catalyst comprises up to 5 wt % of the alkali metal element based on the total weight of the support.

B46. The process of any of B2 to B45, wherein m, n, p, and q are each equal to 1, 2, 15, or 30, or wherein m=1, n=15, p=15, and q=1.

B47. The process of any of B2 to B46, wherein a molar ratio of a combined amount of any Group 2 element, any Group 4 element, any Group 12 element, and any element having an atomic number of 21, 39, or 57-71 to the Group 8-10 element in the catalyst is at least 0.18, at least 0.19, at least 0.24, or at least 0.29.

B48. The process of any of B2 to B47, wherein the support in the catalyst further comprises at least one compound comprising at least one metal element or metalloid element selected from Groups 5, 6, 7, 11, 13, 14, 15, and 16.

B49. The process of any of B2 to B48, wherein at least a portion of any Group 2 element, at least a portion of any Group 4 element, at least a portion of any Group 12 element, and at least a portion of any element having an atomic number of 21, 39, or 57-71 present in the support is an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide.

B50. The process of any of B2 to B49, wherein the support comprises one or more of the following: $Mg_uZn_{1-u}O$, where u is a positive number; $Zn_vAl2O3_{+v}$, where v is a positive number; $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number; BeO; MgO; CaO; BaO; SrO; $BeCO_3$; $MgCO_3$; $CaCO_3$; $SrCO_3$; $BaCO_3$; $ZrO_2$; ZrC; ZrN; $ZrSiO_4$; $CaZrO_3$; $Ca_7ZrAl_6O_{18}$; $TiO_2$; TiC; TiN; $TiSiO_4$; $CaTiO_3$; $Ca_7Al_6O_{18}$; $HfO_2$; HfC; HfN; $HfSiO_4$; $HfZrO_3$; $Ca_7HfAl_6O_{18}$; ZnO; $Zn_3(PO_4)_2$; $Zn(ClO_3)_2$; $ZnSO_4$; $B_2O_6Zn_3$; $Zn_3N_2$; $ZnCO_3$; $CeO2$; $Y_2O_3$; $La_2O_3$; $Sc_2O_3$; $Pr_6O_{11}$; $CePO_4$; $CeZrO_4$; $CeAlO_3$; $BaCeO_3$; $CePO_4$; Yttria-stabilized $ZrO_2$; combinations thereof, and mixtures thereof.

B51. The process of any of B2 to B50, wherein the support further comprises one or more of the following: $B_2O_3$, $Al_2O_3$, $SiO_2$, SiC, $Si_3N_4$, an aluminosilicate, VO, $V_2O_3$, $VO_2$, $V_2O_5$, $Ga_2O_3$, $In_2O_3$, $Mn_2O_3$, $Mn_3O_4$, MnO, a zeolite; combinations thereof; and mixture thereof.

B52. The process of any of B1 to B51, wherein the Group 8-10 element comprises Pt.

B53. The process of any of B1 to B52, wherein the hydrocarbon-containing feed comprises ethane, propane, isobutane, butane, ethylbenzene, propylbenzene, methylethylbenzene, or a mixture thereof.

B54. The process of any of B1 to B53, wherein, during normal operation, the oxidant contacts the coked catalyst during the regeneration interval at a normal temperature, a normal pressure, and for a normal period of time, the process further comprising every 12 hours to 90 days modifying the regeneration interval by increasing the normal temperature, increasing the normal pressure, increasing the normal period of time, or a combination thereof to effect a re-activation of the coked catalyst.

B55. The process of any of B1 to B54, wherein the support comprises ≥3 wt %, ≥6 wt %, ≥11 wt %, ≥15 wt %, or ≥20 wt % of a Group 2 element.

B56. The process of B55, wherein the Group 2 element comprises Mg.

B57. The process of any of B1 to B56, wherein the support comprises calcined hydrotalcite.

B58. The process of any of B1 to B57, wherein the reaction zone is a first reaction zone and the catalyst is a first catalyst, the process further comprising: carrying out the reaction interval, the regeneration interval, and the reduction interval in a second reaction zone comprising a second catalyst; and carrying out the reaction interval, the regeneration interval, and the reduction interval in a third reaction zone comprising a third catalyst, wherein the first reaction zone, the second reaction zone, and the third reaction zone are operated in parallel, and wherein a timing of the reaction interval, the regeneration interval, and the reduction interval between the first, second, and third reaction zones is such that there is a continuous production of the one or more upgraded hydrocarbons and molecular hydrogen across the first, second, and third reaction zones.

B59. The process of B58, wherein the first catalyst, the second catalyst, and the third catalyst have the same composition.

B60. The process of any of B1 to B59, wherein the reducing gas and the regenerated catalyst are contacted for a time period of 0.1 seconds to 90 minutes.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for upgrading a hydrocarbon, comprising:
   (I) introducing a hydrocarbon-containing feed comprising one or more of $C_2$-$C_{16}$ linear or branched alkanes, one or more of $C_4$-$C_{16}$ cyclic alkanes, one or more of $C_8$-$C_{16}$ alkyl aromatics, or a mixture thereof into a reaction zone;
   (II) contacting the hydrocarbon-containing feed with a catalyst disposed within the reaction zone to effect at least one of dehydrogenation, dehydroaromatization, and dehydrocyclization of at least a portion of the hydrocarbon-containing feed to produce a coked catalyst and a first effluent comprising one or more upgraded hydrocarbons and molecular hydrogen, wherein the hydrocarbon-containing feed and the catalyst are contacted at a temperature in a range from 300° C. to 900° C., for a time period of 1 minute to 90 minutes, and under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed, wherein the hydrocarbon-containing feed and the catalyst are contacted in the presence of steam in an amount from 0.1 vol % to 40 vol %, based on a total volume of any $C_2$-$C_{16}$ alkanes, and any $C_8$-$C_{16}$ alkyl aromatics in the hydrocarbon-containing feed, wherein the catalyst comprises a Group 8-10 element or a compound thereof disposed on a support, and wherein the support comprises a mixed Mg/Al metal oxide having a molar ratio of Mg to Al in a range from 1:1 to 10:1;
   (III) halting introduction of the hydrocarbon-containing feed into the reaction zone;
   (IV) introducing an oxidant into the reaction zone;
   (V) contacting the oxidant with the coked catalyst to effect combustion of at least a portion of the coke to produce a regenerated catalyst lean in coke and a second effluent comprising a combustion gas, wherein the oxidant and the coked catalyst are contacted for a time period of 1 minute to 90 minutes;
   (VI) halting introduction of the oxidant into the reaction zone;
   (VII) introducing a reducing gas into the reaction zone;
   (VIII) contacting the reducing gas with the regenerated catalyst to produce a regenerated and reduced catalyst and a third effluent, wherein the reducing gas and the regenerated catalyst are contacted for a time period of 0.1 seconds to 90 minutes;
   (IX) halting introduction of the reducing gas into the reaction zone;
   (X) introducing an additional quantity of the hydrocarbon-containing feed into the reaction zone; and
   (XI) contacting the additional quantity of the hydrocarbon-containing feed with the regenerated and reduced catalyst to produce a re-coked catalyst and additional first effluent, wherein the additional quantity of the hydrocarbon-containing feed and the regenerated and reduced catalyst are contacted at a temperature in a range from 300° C. to 900° C., for a time period of 1 minute to 90 minutes, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed, wherein the additional quantity of the hydrocarbon-containing feed and the catalyst are contacted in the presence of steam in an amount from 0.1 vol % to 40 vol %, based on a total volume of any $C_2$-$C_{16}$ alkanes, and any $C_8$-$C_{16}$ alkyl aromatics in the additional quantity of the hydrocarbon-containing feed.

2. The process of claim 1, wherein an inverse temperature profile or an isothermal temperature profile is maintained within the reaction zone during step (II).

3. The process of claim 1, wherein the catalyst is disposed in a fixed bed within the reaction zone.

4. The process of claim 1, wherein step (IV) further comprises:
   introducing a fuel with the oxidant into the reaction zone; and
   combusting at least a portion of the fuel within the reaction zone to produce heat that heats the reaction zone to a temperature of ≥ 580° C.

5. The process of claim 1, wherein the oxidant is at a temperature in a range from 580° C. to 1,100° C. and at a pressure in a range from 20 kPa-absolute to 1,000 kPa-absolute when contacted with the coked catalyst, and wherein the reducing gas is at a temperature in a range from 450° C. to 900° C. when contacted with the regenerated catalyst.

6. The process of claim 1, wherein the catalyst further comprises up to 10 wt % of a promoter disposed on the support based on the weight of the support, and wherein the promoter comprises Sn.

7. The process of claim 1, wherein the catalyst further comprises up to 5 wt % of an alkali metal element disposed on the support based on the weight of the support.

8. The process of claim 1, wherein, during normal operation, the oxidant contacts the coked catalyst in step (V) at a normal temperature, a normal pressure, and for a normal period of time, the process further comprising every 12 hours to 90 days modifying step (V) by increasing the normal temperature, increasing the normal pressure, increasing the normal period of time, or a combination thereof to effect a re-activation of the coked catalyst.

9. The process of claim 1, wherein the reaction zone is a first reaction zone and the catalyst is a first catalyst, the process further comprising:
carrying out steps (I)-(XI) within a second reaction zone comprising a second catalyst; and
carrying out steps (I)-(XI) within a third reaction zone comprising a third catalyst, wherein the first reaction zone, the second reaction zone, and the third reaction zone are operated in parallel, and wherein a timing of the steps (I)-(XI) between the first, second, and third reaction zones is such that there is a continuous production of the one or more upgraded hydrocarbons and molecular hydrogen across the first, second, and third reaction zones.

10. The process of claim 1, wherein:
the time period the hydrocarbon-containing feed and the catalyst are contacted in step (II) is from 1 minute to 30 minutes,
the time period the oxidant and the coked catalyst are contacted in step (V) is from 1 minute to 30 minutes,
the time period the reducing gas and the regenerated catalyst are contacted in step (VIII) is from 0.1 seconds to 30 minutes, and
the time period the additional quantity of the hydrocarbon-containing feed and the regenerated and reduced catalyst are contacted in step (XI) is from 1 minute to 30 minutes.

11. The process of claim 10, wherein a cycle time from the contacting the hydrocarbon-containing feed with the catalyst in step (II) to the contacting the additional quantity of the hydrocarbon-containing feed with the regenerated and reduced catalyst in step (XI) is <90 minutes.

12. The process of claim 11, wherein:
the catalyst further comprises up to 10 wt % of a promoter disposed on the support based on the weight of the support,
the promoter comprises Sn,
the catalyst comprises 0.001 wt % to 6 wt % of the Group 8-10 element or the compound thereof based on the weight of the support,
the Group 8-10 element comprises Pt, and
the molar ratio of Mg to Al is in a range from 2:1 to 10:1.

13. The process of claim 1, wherein the hydrocarbon-containing feed and the catalyst are contacted in the presence of steam in an amount from 0.1 vol % to 30 vol %, based on a total volume of any $C_2$-$C_{16}$ alkanes and any $C_8$-$C_{16}$ alkyl aromatics in the hydrocarbon-containing feed.

14. The process of claim 1, wherein the hydrocarbon-containing feed and the catalyst are contacted in the presence of steam in an amount from 0.1 vol % to 20 vol %, based on a total volume of any $C_2$-$C_{16}$ alkanes and any $C_8$-$C_{16}$ alkyl aromatics in the hydrocarbon-containing feed.

15. The process of claim 1, wherein the time period the oxidant contacts the coked catalyst in step (V) is at least 20 minutes.

16. The process of claim 1, wherein the hydrocarbon-containing feed has a hydrocarbon partial pressure of 150 kPa-absolute to 1,000 kPa-absolute.

17. The process of claim 1, wherein step (II) further comprises contacting the hydrocarbon-feed with a heat generating material disposed within the reaction zone to generate heat within the reaction zone, wherein the heat generating material comprises an alkaline earth metal, copper, vanadium, cerium, yttrium, scandium, manganese, silver, bismuth, or a mixture or combination thereof.

18. The process of claim 1, wherein the molar ratio of Mg to Al is in a range from 2:1 to 10:1.

19. The process of claim 1, wherein:
the catalyst further comprises 0.5 wt % to 2 wt % of a promoter comprising Sn disposed on the support based on the weight of the support,
the catalyst comprises ≤0.045 wt % of the Group 8-10 element or the compound thereof based on the weight of the support,
the Group 8-10 element comprises Pt, and
the molar ratio of Mg to Al is in a range from 2:1 to 10:1.

20. The process of claim 19, wherein the catalyst comprises ≤0.04 wt % of the Group 8-10 element.

21. The process of claim 19, wherein the catalyst comprises ≤0.03 wt % of the Group 8-10 element.

22. The process of claim 1, further comprising repeating steps (III) to (XI) for at least 15 cycles, wherein:
the catalyst further comprises up to 10 wt % of a promoter comprising Sn disposed on the support, based on the weight of the support,
the catalyst comprises 0.001 wt % to 6 wt % of the Group 8-10 element or the compound thereof based on the weight of the support,
the Group 8-10 element comprises Pt, and
the additional first effluent produced in the fifteenth cycle has an upgraded hydrocarbon product yield that is at least 90% of an upgraded hydrocarbon product yield in the first effluent produced in the first cycle.

23. The process of claim 22, wherein the hydrocarbon-containing feed comprises propane and the one or more upgraded hydrocarbons comprise propylene.

24. The process of claim 23, wherein:
in step (II) the hydrocarbon-containing feed and the catalyst are contacted in the presence of steam in an amount from 0.1 vol % to 20 vol %, based on the total volume of any $C_2$-$C_{16}$ alkanes, and any $C_8$-$C_{16}$ alkyl aromatics in the hydrocarbon-containing feed,
the time period in step (II) is less than 20 minutes,
in step (XI) the additional quantity of the hydrocarbon-containing feed and the catalyst are contacted in the presence of steam in an amount from 0.1 vol % to 20 vol %, based on the total volume of any $C_2$-$C_{16}$ alkanes, and any $C_8$-$C_{16}$ alkyl aromatics in the additional quantity of the hydrocarbon-containing feed,
the time period in step (XI) is less than 20 minutes, and
contacting the hydrocarbon-containing feed with the catalyst in step (II) and contacting the additional quantity of the hydrocarbon-containing feed with the regenerated and reduced catalyst in step (XI) during the fifteenth cycle each have an average propylene yield of ≥50% and an average propylene selectivity of ≥85%.

25. A cyclic process for upgrading a hydrocarbon in a reactor system, comprising:
- (I) a reaction interval comprising introducing and halting introduction of a hydrocarbon-containing feed into a reaction zone, wherein the hydrocarbon-containing feed comprises one or more of $C_2$-$C_{16}$ linear or branched alkanes, one or more of $C_4$-$C_{16}$ cyclic alkanes, one or more of $C_8$-$C_{16}$ alkyl aromatics, or a mixture thereof;
- (II) a regeneration interval following the reaction interval, the regeneration interval comprising introducing and halting introduction of an oxidant into the reaction zone; and
- (III) a reduction interval following the regeneration interval, the reduction interval comprising introducing and halting introduction of a reducing gas into the reaction zone; wherein:
  - the reaction interval is restarted after the reduction interval;
  - during introduction of the hydrocarbon-containing feed into the reaction zone, the hydrocarbon-containing feed contacts a catalyst disposed within the reaction zone to effect at least one of dehydrogenation, dehydroaromatization, and dehydrocyclization of at least a portion of the hydrocarbon-containing feed to produce a coked catalyst and a first effluent comprising one or more upgraded hydrocarbons and molecular hydrogen, wherein the hydrocarbon-containing feed and the catalyst are contacted at a temperature in a range from 300° C. to 900° C., for a time period of 1 minute to 90 minutes, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed, and wherein the hydrocarbon-containing feed and the catalyst are contacted in the presence of steam at in amount from 0.1 vol % to 40 vol %, based on a total volume of any $C_2$-$C_{16}$ alkanes, and any $C_8$-$C_{16}$ alkyl aromatics in the hydrocarbon-containing feed;
  - during introduction of the oxidant into the reaction zone, the oxidant contacts the coked catalyst to effect combustion of at least a portion of the coke to produce a regenerated catalyst lean in coke and a second effluent comprising a combustion gas, wherein the oxidant and the coked catalyst are contacted for a time period of 1 minute to 90 minutes;
  - during introduction of the reducing gas into the reaction zone, the reducing gas contacts the regenerated catalyst to produce a regenerated and reduced catalyst;
  - the catalyst comprises a Group 8-10 element or a compound thereof disposed on a support; and
  - the support comprises a mixed Mg/Al metal oxide having a molar ratio of Mg to Al in a range from 1:1 to 10:1.

26. The process of claim 25, wherein:
steps (I) to (III) are repeated for at least 15 cycles,
the catalyst further comprises up to 10 wt % of a promoter comprising Sn disposed on the support, based on the weight of the support,
the catalyst comprises 0.001 wt % to 6 wt % of the Group 8-10 element or the compound thereof based on the weight of the support,
the Group 8-10 element comprises Pt, and
the first effluent produced in step (I) of the fifteenth cycle has an upgraded hydrocarbon product yield that is at least 90% of an upgraded hydrocarbon product yield in the first effluent produced in step (I) of the first cycle.

* * * * *